United States Patent
Fernandes

(10) Patent No.: US 9,861,616 B2
(45) Date of Patent: Jan. 9, 2018

(54) METHODS FOR TREATING RESPIRATORY DISEASES AND FORMULATIONS THEREFOR

(71) Applicant: CEMPRA PHARMACEUTICALS, INC., Chapel Hill, NC (US)

(72) Inventor: Prabhavathi Fernandes, Chapel Hill, NC (US)

(73) Assignee: CEMPRA PHARMACEUTICALS, INC., Chapel Hill, NC (US)

( * ) Notice: Subject to any disclaimer, the term of this patent is extended or adjusted under 35 U.S.C. 154(b) by 0 days.

(21) Appl. No.: 14/774,788

(22) PCT Filed: Mar. 14, 2014

(86) PCT No.: PCT/US2014/027214
§ 371 (c)(1),
(2) Date: Sep. 11, 2015

(87) PCT Pub. No.: WO2014/152326
PCT Pub. Date: Sep. 25, 2014

(65) Prior Publication Data
US 2016/0030396 A1 Feb. 4, 2016

Related U.S. Application Data

(60) Provisional application No. 61/781,197, filed on Mar. 14, 2013.

(51) Int. Cl.
| | | |
|---|---|---|
| A01N 43/76 | (2006.01) |
| A61K 31/42 | (2006.01) |
| A61K 31/424 | (2006.01) |
| A61K 9/00 | (2006.01) |
| A61K 45/06 | (2006.01) |

(52) U.S. Cl.
CPC .......... *A61K 31/424* (2013.01); *A61K 9/007* (2013.01); *A61K 9/0075* (2013.01); *A61K 9/0078* (2013.01); *A61K 45/06* (2013.01)

(58) Field of Classification Search
None
See application file for complete search history.

(56) References Cited

U.S. PATENT DOCUMENTS

| | | |
|---|---|---|
| 1,354,753 A | 10/1920 | Howard |
| 2,180,006 A | 11/1939 | Hasche |
| 3,668,282 A | 6/1972 | Below |
| 3,843,787 A | 10/1974 | Fabrizio |
| 4,312,866 A | 1/1982 | Caruso |
| 4,331,803 A | 5/1982 | Watanabe |
| 4,474,768 A | 10/1984 | Bright |
| 4,742,049 A | 5/1988 | Baker |
| 4,886,792 A | 12/1989 | Djokic |
| 4,990,602 A | 2/1991 | Morimoto |
| 5,211,955 A | 5/1993 | Legros |
| 5,444,051 A | 8/1995 | Agouridas |
| 5,527,780 A | 6/1996 | Agouridas |
| 5,543,400 A | 8/1996 | Agouridas |
| 5,614,614 A | 3/1997 | Agouridas |
| 5,635,485 A | 6/1997 | Agouridas |
| 5,656,607 A | 8/1997 | Agouridas |
| 5,747,467 A | 5/1998 | Agouridas |

(Continued)

FOREIGN PATENT DOCUMENTS

| | | |
|---|---|---|
| CN | 1343216 A | 4/2002 |
| CN | 1354753 | 6/2002 |

(Continued)

OTHER PUBLICATIONS

Lyczak, et. al., Clin. Microbiol. Rev. 2002; 15(2) pp. 194-222.*
PCT Search Report prepared for PCT/US2014/027214 dated Jul. 18, 2014.
Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,. beta.-unsaturated ketone." The Journal of Organic Chemistry 53.10 (1988): 2340-2345.
Ashizawa, Kazuhide, "Physico-Chemical Studies on the molecular Details of Drug Crystals," Phar Tech Japan, 2002, vol. 18, No. 10. pp. 81-96.

(Continued)

*Primary Examiner* — Jeffrey H Murray
(74) *Attorney, Agent, or Firm* — Brannon Sowers & Cracraft PC

(57) ABSTRACT

Compounds of formula (I), compositions comprising them, and methods and uses thereof are described herein for the treatment of respiratory diseases, including cystic fibrosis. Inhalation formulations of macrolide antibiotics are also described herein. The treatment of bacterial infections continues to be an important endeavor of pharmaceutical research and development. The specter of bacterial resistance to currently available antibiotics is ever-present, and accordingly, new and improved compounds, pharmaceuticals formulations, treatment methods, and treatment protocols are needed.

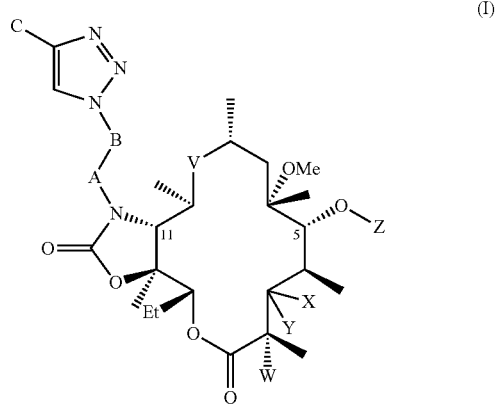

27 Claims, 3 Drawing Sheets

(56) References Cited

U.S. PATENT DOCUMENTS

| | | |
|---|---|---|
| 5,760,233 A | 6/1998 | Agouridas |
| 5,770,579 A | 6/1998 | Agouridas |
| 5,834,428 A | 11/1998 | Drucker |
| 5,985,844 A | 11/1999 | Heck |
| 6,011,142 A | 1/2000 | Bonnet |
| 6,020,521 A | 2/2000 | Randolph |
| 6,028,181 A | 2/2000 | Or |
| 6,096,714 A | 8/2000 | Agouridas |
| 6,096,922 A | 8/2000 | Lal |
| 6,121,432 A | 9/2000 | Bonnet |
| 6,270,768 B1 | 8/2001 | OConnell |
| 6,313,101 B1 | 11/2001 | Denis |
| 6,395,300 B1 | 5/2002 | Straub |
| 6,395,710 B1 | 5/2002 | Chu |
| 6,407,074 B1 | 6/2002 | Bronk |
| 6,407,257 B1 | 6/2002 | Agouridas et al. |
| 6,420,535 B1 | 7/2002 | Phan |
| 6,437,106 B1 | 8/2002 | Stoner |
| 6,440,941 B1 | 8/2002 | Denis |
| 6,455,505 B2 | 9/2002 | Agouridas |
| 6,515,116 B2 | 2/2003 | Suh |
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,163,924 B2 | 1/2007 | Burger |
| 7,332,476 B2 | 2/2008 | Burger |
| 7,375,234 B2 | 5/2008 | Sharpless |
| 7,419,961 B2 | 9/2008 | Napoletano |
| 7,601,695 B2 * | 10/2009 | Liang ............... C07H 17/08 514/29 |
| 8,012,943 B2 * | 9/2011 | Duffield ............ C07H 17/08 514/29 |
| 8,247,394 B2 | 8/2012 | Fernandes |
| 8,343,936 B2 * | 1/2013 | Duffield ............ C07H 17/08 514/29 |
| 8,791,080 B2 | 7/2014 | Fernandes |
| 8,796,232 B2 | 8/2014 | Fernandes |
| 9,051,346 B2 | 6/2015 | Pereira |
| 9,200,026 B2 * | 12/2015 | Liang ............... C07H 17/08 |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1 | 1/2005 | Burger et al. |
| 2005/0014706 A1 | 1/2005 | Falzari |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0076536 A1 | 4/2006 | Barshied |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1 | 5/2008 | Ivezic |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0005325 A1 | 1/2009 | Bas |
| 2009/0075916 A1 | 3/2009 | Upadhyay |
| 2009/0076253 A1 | 3/2009 | Kashimura |
| 2009/0087389 A1 | 4/2009 | Leonard |
| 2009/0131389 A1 | 5/2009 | Jensen |
| 2009/0156517 A1 | 6/2009 | Zhang |
| 2009/0209547 A1 | 8/2009 | Kim |
| 2010/0216731 A1 | 8/2010 | Pereira |
| 2011/0119604 A1 | 5/2011 | Lo |
| 2011/0195920 A1 | 8/2011 | Fernandes |
| 2012/0071429 A1 | 3/2012 | Duffield |
| 2012/0172323 A1 | 7/2012 | Fernandes |
| 2012/0231995 A1 | 9/2012 | Beck |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0102523 A1 | 4/2013 | Bartizal |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| CN | 101045063 | 10/2007 |
| EP | 0248279 A2 | 12/1987 |
| EP | 0680967 A1 | 11/1995 |
| EP | 1024145 A2 | 8/2000 |
| EP | 1167375 | 1/2002 |
| GB | 891817 | 3/1962 |
| JP | S59175414 | 10/1984 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008526948 | 7/2008 |
| JP | 2008534504 | 8/2008 |
| JP | 2009500356 | 1/2009 |
| JP | 2009502788 | 1/2009 |
| JP | 5914335 | 5/2016 |
| RU | 2230748 | 6/2004 |
| WO | 9736912 | 10/1997 |
| WO | 9830574 A1 | 7/1998 |
| WO | 9856800 A1 | 12/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |
| WO | 0062783 A2 | 10/2000 |
| WO | 0110878 A1 | 2/2001 |
| WO | 0250092 A1 | 6/2002 |
| WO | 03004509 | 1/2003 |
| WO | 03004509 A2 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 2007143507 | 12/2007 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011032052 | 3/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |

(56) References Cited

FOREIGN PATENT DOCUMENTS

| WO | 2014152326 | 9/2014 |
|---|---|---|
| WO | 2014165792 | 10/2014 |
| WO | 2015123256 | 8/2015 |
| WO | 2015181723 | 12/2015 |
| WO | 2016022658 | 2/2016 |
| WO | 2016144833 | 9/2016 |

OTHER PUBLICATIONS

Barcia-Macay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp. 841-851.

Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).

Berge, Stephen M., et al., "Pharmaceutical Salts", 1977, Journal of Pharmaceutical Sciences, vol. 66, No. 1, pp. 1-19.

Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.

Bermudez, Luiz E., et al., "Telithromycin is Active Against *Mycobacterium avium* in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.

Caira MR, "Crystalline polymorphism of orgainic compounds," Design of Organic Solids, Topics in Current Chemistry, Springer Berlin Heidelberg, 1998, p. 163-208.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.

Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.

Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.

Champney et al., 'Structure-Activity Relationships for Six Ketolide Antibiotics', Current Microbiology, 42:203-10 (2001).

Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).

Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).

Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.

Duffy, L., et al., Fluoroquinolone resistance in Ureaplasma parvum in the United States, J Clin Microbiol 44:1590-1591 (2006).

European Search Report for EP 09 82 2827, dated Mar. 21, 2012.

Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.

Hancock, Bruno C., Sheri L. Shamblin, and George Zografi. "Molecular mobility of amorphous pharmaceutical solids below their glass transition temperatures." Pharmaceutical research 12.6 (1995): 799-806.

Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.

Holzer, G., et al., "Ka1,2 and KB1,3 X-Ray Emission Lines of the 3d Transition Metals", Dec. 1997, Physical Review, vol. 56, No. 6, pp. 4554-4568.

Inglesby, Thomas V., et al., "Anthrax as a Biological Weapon, 2002", 2002, Journal of the American Medical Association, vol. 287, No. 17, pp. 2236-2252.

International Search Report for PCT/US2009/061977, dated Dec. 23, 2009, (3 pages).

Jones et al.: 'MIC Quality Control Guidelines and Disk Diffusion Test Optimization for CEM-101, a Novel Fluoroketolide' Journal of Clinical Microbiology vol. 48, No. 4, Dec. 30, 2009, pp. 1470-1473.

International Search Report Written Opinion for PCT/US2008/080936 completed Dec. 8, 2008.

Katz, Leonard, and Gary W. Ashley. "Translation and protein synthesis: macrolides." Chemical reviews 105.2 (2005): 499-528.

Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).

Laine, Loren, et al., "Prospective comparison of H&E, Giemsa and Genta stains for the diagnosis of Helicobacter pylori," 1997, Gastrointestinal Endoscopy, vol. 45, No. 6, pp. 463-467.

Lee, Adrian, et al., "A standard mouse model of Helicobacter pylori infection: introducing the Sydney Strain," 1997, Gastroenterology, vol. 112, pp. 1386-1397.

Lemaire, Sandrine, et al., "Cellular Accumulation and Pharmacodynamic Evaluation of the Intracellular Activity of CEM-101, a Novel Fluoroketolide, Against *Staphylococcus aureus*, Listeria Monocytogenes and Legionella Pneumophila in Human THP-1 Macrophages", 2009, Antimicrobial Agents and Chemotherapy. vol. 53, No. 9, pp. 3734-3743.

LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.

Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.

Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.

Li, X., et al., Emerging macrolide resistance in Mycoplasma pneumoniae in children: detection and characterization of resistant isolates, Pediatr Infect Dis J, 28:693-696 (2009).

Or et al., 'Design, Synthesis, and Antimicrobial Activity of 6-0-Substituted Ketolides Active Against Resistant Respiratory Tract Pathogens', J. Med. Chem., 43:1045-49 (2000).

Organic Compounds Crystal Manufacture Handbook—Principles and Knowhow, 2008, pp. 57 to 84.

Patel, Ramesh N., "Stereoselective Biocatalysis", 2000, Bristol-Myers Squibb Research Institute; pp. 775-797.

Pathak et al., "Enzymatic Protecting Group Techniques in Organic Synthesis," Stereosel, Biocatal., 2000; pp. 775-797.

PCT International Search Report and Written Opinion for PCT/US2011/029424, dated May 25, 2011.

PCT Search Report/Written Opinion prepared for PCT/US2010/048540, dated Oct. 21, 2010.

PCT Search Report and Written Opinion for PCT/US2011/037330 completed Aug. 26, 2011.

(56) References Cited

OTHER PUBLICATIONS

Petit, Samuel, and Gérard Coquerel. "The amorphous state." Polymorphism: In the Pharmaceutical Industry 10 (2006): 1.
PCT Search Report and Written Opinion prepared for PCT/US2009/061978 dated Dec. 9, 2009.
Physicians' Desk Reference, p. 2905, (2007).
Plata, Daniel J., et al. "The synthesis of ketolide antibiotic ABT-773 (cethromycin)." Tetrahedron 60.45 (2004): 10171-10180.
Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Romero et al., 'An efficient entry to new sugar modified ketolide antibiotics' Tetrahedron Letters, vol. 46, 2005, pp. 1483-1487.
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Threlfall, Terence L. "Analysis of organic polymorphs. A review." Analyst 120.10 (1995): 2435-2460.
Vennerstrom, Jonathan L., et al., "Identification of an Antimalarial Synthetic Trioxolane Drug Development Candidate", 2004, Letters to Nature, vol. 430, pp. 900-904.
Vince, R., Almquist, R. G., Ritter, C. L., and Daluge, S., Antimicrobial Agents and Chemotherapy, vol. 8, No. 4, 1975, 439-443.
Waites, K.B., et al., Mycoplasmas and ureaplasmas as neonatal pathogens, Clin Microbiol Rev 18:757-89 (2005).
Zhenkun Ma & Peter A. Nemoto "Discovery and Development of Ketolides as a New Generation of MacrolideAntimicrobial Agents" Curr Med Chem—Anti-Infective Agents 1:15-34 (2002).
Zuckerman, "Macrolides and ketolides: azithromycin, clarithromycin, telithromycin", Infectious Disease Clinics of North America, vol. 18, (2004), pp. 621-649.
Sumerkan, B., Aygen, B., Doganay, M., & Sehmen, E. (1996). Antimicrobial susceptibility of Bacillus anthracis against macrolides. Salisbury Med Bull Supplement, 87, 138.
Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides an underappreciated benefit in the treatment of community-acquired respiratory tract infections and chronic inflammatory pulmonary conditions?." Journal of Antimicrobial Chemotherapy 55.1 (2005): 10-21.
de Jong, J. T., et al. "[Large-scale, acute, bacterial gastroenteritis caused by the enterotoxin of *Staphylococcus aureus* after a barbecue]." Nederlands tijdschrift voor geneeskunde 148.43 (2004): 2136-2140.
Raj, Pushker. "Pathogenesis and laboratory diagnosis of *Escherichia coli* associated enteritis." Clinical microbiology Newsletter 15.12 (1993): 89-93.
Ikeue, T., et al. "[Pneumonia caused by Nocardia nova]." Nihon Kokyuki Gakkai zasshi=the journal of the Japanese Respiratory Society 39.7 (2001): 492-497.
Thakkar, Shyam, and Radheshyam Agrawal. "A case of *Staphylococcus aureus* enterocolitis: a rare entity." Gastroenterology & hepatology 6.2 (2010): 115-117.
Wain, Harry, and Paul A. Blackstone. "Staphylococcal Gastroenteritis." The American journal of digestive diseases 1.10 (1956): 424.
Boyce, Thomas G., "Staphylococcal Food Poisoning," Merck Manuals (2015) 2 pages.
Lv Yang et al., "Polymorphic Drugs." Oct. 31, 2009, pp. 110-111.
Maurin, M., Mersali, N. F., & Raoult, D. (2000). Bactericidal activities of antibiotics against intracellular Francisella tularensis. Antimicrobial agents and chemotherapy, 44(12), 3428-3431.
Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated microbroth dilution and Etest® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.
Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-0-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against *Mycobacterium tuberculosis*. Tuberculosis, 88, S49-S63.
Putnam S. D. et al, Antimicrobial Characterization of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U: Intellectual Property Office of Singapore; dated Mar. 31, 2015, 6 pages.
Database WPI Week 200822 Thomson Scientific, London, GB; AN 2008-D02982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Le Loir, Yves, Florence Baron, and Michel Gautier. "*Staphylococcus aureus* and food poisoning." Genet Mol Res 2.1 (2003): 63-76.
Brittain HG editor "Polymorphism in pharmaceutical solids", Chapter 1, p. 1-10 (Grant DJW) and Chapter 5, p. 183-226 (1999).
Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.
Cotter, Paul D., and Colin Hill. "Surviving the acid test: responses of gram-positive bacteria to low pH." Microbiology and Molecular Biology Reviews 67.3 (2003): 429-453.
Wain, Harry, and Paul A. Blackstone. "Staphylococcal Gastroenteritis." The American journal of digestive diseases 1.10 (1956): 424-429.

(56) References Cited

OTHER PUBLICATIONS

Lyczak, J. B., Cannon, C. L., & Pier, G. B. (2002). Lung infections associated with cystic fibrosis. Clinical microbiology reviews, 15(2), 194-222.

Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.

Bryskier, A. "Ketolides telithromycin, an example of a new class of antibacterial agents." Clinical Microbiology and Infection 6.12 (2000): 661-669.

Morimoto, Shigeo, et al. "Chemical modification of erythromycins. I. Synthesis and antibacterial activity of 6-O-methylerythromycins A." The Journal of antibiotics 37.2 (1984): 187-189.

Hällgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.

Fernandes, P., et al. Intravenous Formulation of Solithromycin, a Painless Macrolide Antibiotic in a Rabbit Intravenous Injection Model, 2011, 5 pages.

Allen Loyd V Jr, Acidifying Agents, Featured Excipient. International Journal of Pharmaceutical Compounding, Dec. 31, 1999, vol. 3, No. 4, pp. 309 (abstract only).

Yatin R. G. et al., Excipients for Protein Drugs. Excipient Development for Pharmaceutical, Biotechnology, and Drug Delivery Systems, Jul. 28, 2006, pp. 299-300.

Fernandes, P., et al. "Solithromycin Macrolide Antibiotic." Drugs of the Future 36.10 (2011): 751-758.

Raoul, Jennifer M., Marc R. Peterson, and Theresa C. Peterson. "A novel drug interaction between the quinolone antibiotic ciprofloxacin and a chiral metabolite of pentoxifylline." Biochemical pharmacology 74.4 (2007): 639-646.

Balzer, W. (2005). Antimicrobial-resistant gram-positive bacteria in PD peritonitis and the newer antibiotics used to treat them. Peritoneal Dialysis International, 25(4), 313-319.

\* cited by examiner

METHODS FOR TREATING RESPIRATORY DISEASES AND FORMULATIONS THEREFOR

CROSS-REFERENCE TO RELATED APPLICATION

This application is a U.S. national application under 37 C.F.R. §371(b) of International Application Serial No. PCT/US2014/027214 filed on Mar. 14, 2014, which claims the benefit under 35 U.S.C. §119(e) of U.S. Provisional Application No. 61/781,197, filed on Mar. 14, 2013, the entire disclosures of which are incorporated herein by reference.

TECHNICAL FIELD

The invention described herein pertains to the treatment of respiratory diseases, including cystic fibrosis. The invention described herein also pertains to inhalation formulations of macrolide antibiotics.

BACKGROUND AND SUMMARY OF THE INVENTION

The treatment of bacterial infections continues to be an important endeavor of pharmaceutical research and development. The specter of bacterial resistance to currently available antibiotics is ever-present, and accordingly, new and improved compounds, pharmaceutical formulations, treatment methods, and treatment protocols are needed. In addition, bacterial infections present themselves in a wide range of tissues, and in many cases, those tissues pose particular challenges for successful treatment. For example, new treatments of bacterial infections of the respiratory system, including acute and chronic pulmonary and endobronchial infections, are needed.

Many antibiotics do not achieve sufficiently high lung concentrations to be effectively used in the treatment and/or prophylaxis of acute and chronic pulmonary and endobronchial diseases. For example, aminoglycoside penetration into the bronchial secretions has been reported to be poor, at approximately only about 12% of the peak serum concentration (Rev. Infect. Dis., 3:67 (1981)). In addition, it has been reported that sputum itself is inhibitory to the bioactivity of aminoglycosides because of its high ionic strength and the presence of divalent cations (Advances in Pediatric Infections Diseases, 8:53 (1993)). Sputum also contains mucin glycoproteins and DNA, which bind aminoglycosides. It has also been reported that to overcome the inhibitory activity, the concentration of aminoglycosides in the sputum would need to be increased to about ten times the minimum inhibitory concentration of the particular target pathogen, such as *Pseudomonas aeruginosa* isolates (J. Infect. Dis., 148:1069 (1983)).

It has also been reported that it is particularly difficult to treat cystic fibrosis (CF), a common genetic disease that is characterized by the inflammation and progressive destruction of lung tissue. The debilitation of the lungs in CF patients is associated with accumulation of purulent sputum produced as a result of chronic endobronchial infections caused by pathogenic bacteria, such as *H. influenzae, Staphylococcus aureaus*, and *Pseudomonas aeruginosa*, and the like. Nearly all individuals suffering from CF eventually die of respiratory failure.

Because certain antibiotics, like aminoglycosides, penetrate poorly into the sputum, to achieve therapeutic concentrations in sputum, high dose parenteral administration is required. Such dosing regimens increase the risk of systemic toxicity including ototoxicity and nephrotoxicity because the serum contains high aminoglycoside concentrations. Intravenous therapy may also increase hardship on the patient, and require hospitalization, which increases treatment costs and exposes the patient to potential other infections. It is appreciated that during infection, the bacteria may predominantly reside in the smaller airways, such as the terminal and respiratory bronchioles, and that the bacteria may predominantly colonize in the larger airways. It has also been reported that when azithromycin is administered by inhalation and other intrabronchial routes, the half-life in the pharynx and lungs is undesirably long, leading to a higher potential for resistance.

Tobramycin inhalation solution is currently the only aerosol antibiotic approved for use for the treatment of bacterial infections in patients with CF. It has been reported that the aerosol administration of tobramycin reduces the potential for systemic toxicity. However, it has also been reported that long term use has been associated with multiple-antibiotic-resistant *P. aeruginosa* strains. Thus, there is a need for the development of different treatments, including classes of aerosol antibiotics for the treatment, of chronic lung infections in patients with CF.

It has been unexpectedly discovered that unlike azithromycin, triazole-containing macrolides described herein have an optimal half-life in the pharynx and lungs, which allows for efficacy in treating disease in the lungs with a lower potential for resistance development. It has also been surprisingly discovered that the triazole-containing macrolides described herein may be administered by inhalation, including intranasal and oral inhalation, and other nasal, sinus, respiratory tract, pulmonary, and intrabronchial routes. It has also been unexpectedly discovered that the triazole-containing macrolides described herein exhibit a large volume of distribution.

It has also been discovered that the macrolides described herein are useful in treating respiratory tract infections (RTIs). It has been surprisingly discovered that the compounds described herein also achieve sufficiently high lung levels upon oral administration. Accordingly, methods are described herein for the treatment and/or prophylaxis of acute and chronic pulmonary and endobronchial diseases, where the methods include the step of administering or co-administering one or more macrolides described herein to a host animal. The macrolides may be administered by a variety of routes, including but not limited to oral, parenteral, inhalation, and like routes of administration. Without being bound by theory, it is believed herein that the utility of the macrolides described herein is due at least in part to the unexpectedly high lung tissue levels of the compounds following administration, including oral and parenteral administration. It has also been surprisingly discovered that the compounds do not have to be administered by inhalation to achieve efficacious lung levels.

It has also been discovered that the macrolide compounds described herein are useful in the treatment and/or prophylaxis of acute and chronic pulmonary and endobronchial diseases, such as diseases caused by or exacerbated by bacteria, including *Pseudomonas aeruginosa* seen in CF patients, chronic bronchitis, and bronchiectasis. It has been discovered that the macrolides described herein have potent anti-inflammatory activities, and therefore are useful in treating the inflammatory component of various pulmonary and endobronchial diseases, such as CF.

It has also been discovered that the macrolides described herein may be co-administered with other antibiotics, such as aminoglycosides, fluoroquinolones, aztreonam, fosfomycin, and the like, and that such co-administration give unexpectedly high efficacy. Without being bound by theory, it is believed herein that the unexpectedly high efficacy may be due to one or more properties of the macrolides. One such property may be that the macrolides have been shown to not antagonize the activity of other antibiotics, such as aminoglycoside antibiotics, which has been reported for other antibacterial agents during co-administration. Another such property may be that the macrolides surprisingly synergize the activity of other antibiotics, such as aminoglycoside antibiotics.

It has also been discovered that the macrolides described herein are useful in treating diseases that are caused at least in part by *Escherichia coli, Enterobacteria* species, *Klebsiella pneumoniae, K. oxytoca, Proteus mirabilis, Pseudomonas aeruginosa, Serratia marcescens, Haemophilus influenzae, Burkholderia cepacia, Stenotrophomonas maltophilia, Alcaligenes xylosoxidans*, multidrug resistant *Pseudomonas aeruginosa*. The macrolides may be administered alone or in combination with other antibiotics, such as aminoglycosides, fluoroquinolones, aztreonam, fosfomycin, and the like.

Described herein are compounds, compositions, formulations, uses in the manufacture of medicaments, and methods for treating respiratory infections, and related diseases, including cystic fibrosis (CF), diseases caused at least in part by *Mycobacterium avium* complex (MAC) or *Mycobacterium hominus* (MAH), patients suffering from infection co-morbid with HIV, AIDS and/or AIDS related diseases, and other immunocompromised patients suffering from infection. Without being bound by theory, it is believed herein that efficacy in treating disease such as CF is due at least in part to the combination of antibacterial and anti-inflammatory activity of the compounds administered.

DETAILED DESCRIPTION

Figure 1:
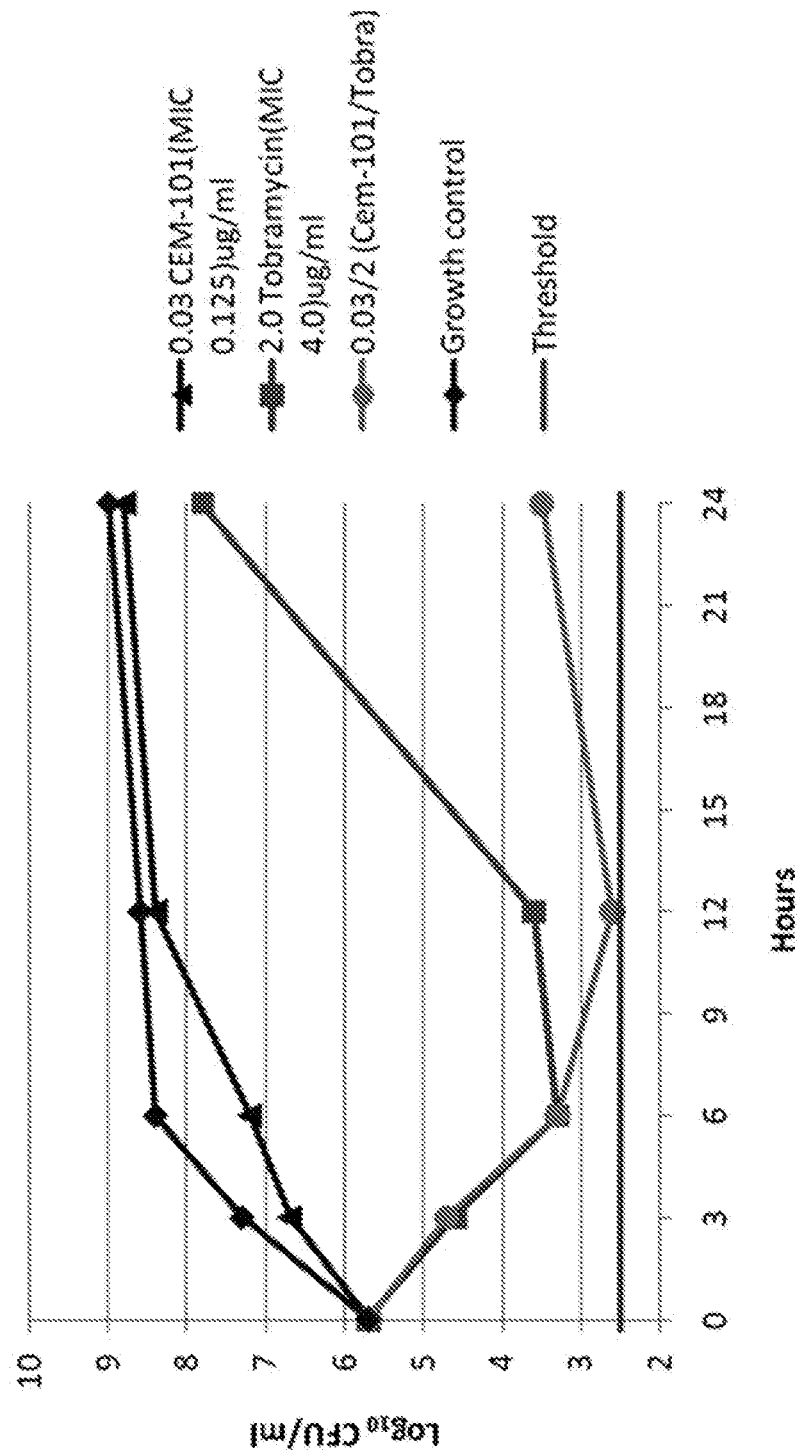
FIG. 1 shows that synergy against MRSA SA 2230 is observed with achievable levels of CEM-101 co-administered with tobramycin.

In one embodiment, the compounds, compositions, formulations, and methods include one or more macrolides described herein. In another embodiment, the compounds, compositions, and formulations are adapted for oral administration. In another embodiment, the compounds, compositions, and formulations are adapted for parenteral administration. In another embodiment, the compounds, compositions, and formulations are adapted for administration by inhalation. In another embodiment, the methods include oral administration. In another embodiment, the methods include parenteral administration. In another embodiment, the methods include administration by inhalation.

It has been unexpectedly discovered herein that the triazole-containing ketolide antibiotics and fluoro derivatives thereof, such as CEM-101 and related compounds, are effective anti-inflammatory agents and as such are effective in treating CF. In particular, triazole-containing ketolide antibiotics and fluoro derivatives thereof described herein are effective in treating the bacterial and inflammatory aspects of CF.

It is also discovered herein that the compounds described herein exhibit high solution stability even during long term storage.

In another embodiment, compounds, compositions, and methods are described herein for treating CF that includes both a bacterial and inflammatory component.

The invention described herein is further illustrated by the following enumerated and non-limiting clauses:

1. A method for treating a pulmonary or endobronchial disease in a host animal, the method comprising the step of administering to the host animal a therapeutically effective amount of one or more compounds of the formula

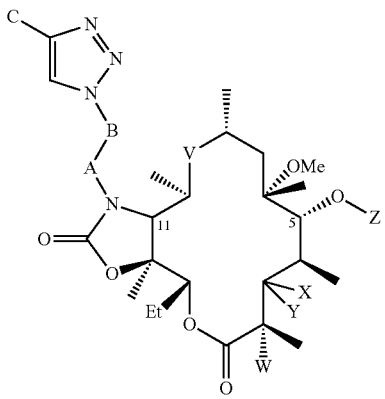

or pharmaceutically acceptable salts thereof, wherein:
X is H; and Y is $OR_7$; where $R_7$ is a monosaccharide or disaccharide, or a derivative thereof; or X and Y are taken together with the attached carbon to form carbonyl;

Z is a monosaccharide or disaccharide, or a derivative thereof;

V is C(O), or C(=NR$_{11}$), wherein R$_{11}$ is hydroxy or alkoxy;

W is H, F, Cl, Br, I, or OH;

A is CH$_2$, C(O), C(O)O, C(O)NH, S(O)$_2$, S(O)$_2$NH, or C(O)NHS(O)$_2$;

B is (CH$_2$)$_n$ where n is an integer in the range from 0 to about 10, or B is C$_2$-C$_{10}$ alkenyl or alkynyl; and C is cycloalkyl, cycloheteroalkyl, aryl, arylalkyl, heteroaryl, or heteroarylalkyl, each of which is optionally substituted;

where the compound is administered by inhalation to the endobronchial space of the patient.

2. A composition for administration by inhalation, the composition comprising one or more compounds of the formula

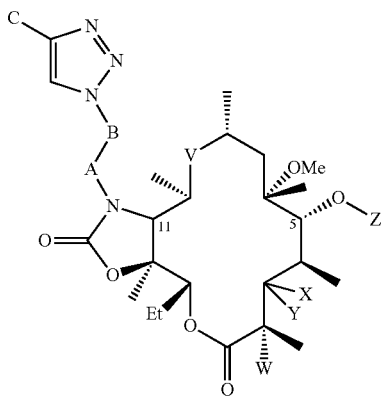

or pharmaceutically acceptable salts thereof, wherein:

X is H; and Y is OR$_7$; where R$_7$ is a monosaccharide or disaccharide, or a derivative thereof; or X and Y are taken together with the attached carbon to form carbonyl;

Z is a monosaccharide or disaccharide, or a derivative thereof;

V is C(O), or C(=NR$_{11}$), wherein R$_{11}$ is hydroxy or alkoxy;

W is H, F, Cl, Br, I, or OH;

A is CH$_2$, C(O), C(O)O, C(O)NH, S(O)$_2$, S(O)$_2$NH, or C(O)NHS(O)$_2$;

B is (CH$_2$)$_n$ where n is an integer in the range from 0 to about 10, or B is C$_2$-C$_{10}$ alkenyl or alkynyl; and C is cycloalkyl, cycloheteroalkyl, aryl, arylalkyl, heteroaryl, or heteroarylalkyl, each of which is optionally substituted.

3. A unit dose of a therapeutically effective amount of the compound or composition of clause 2, the unit dose comprising a predetermined amount of the compound adapted for administering by inhalation.

4. A kit for treating a pulmonary or endobronchial disease in a host animal, the kit comprising a solid unit dose of a therapeutically effective amount of the compound or composition of any one of the preceding clauses, and an aerosolizer adapted or configured to aerosolize the pharmaceutical formulation and deliver it to the lower respiratory tract and pulmonary compartment following intraoral administration, and instructions for use. It is appreciated that the solid unit dose may be administered as a dry powder or a metered-dose inhaler.

5. A kit for treating a pulmonary or endobronchial disease in a host animal, the kit comprising a solid unit dose of a therapeutically effective amount of the compound or composition of any one of the preceding clauses, and an aerosolizer adapted or configured to aerosolize the pharmaceutical formulation and deliver it to the nasal cavity following intranasal administration, and instructions for use. It is appreciated that the solid unit dose may be administered as a dry powder or a metered-dose inhaler.

6. A kit for treating a pulmonary or endobronchial disease in a host animal, the kit comprising a solid unit dose of a therapeutically effective amount of the compound or composition of any one of the preceding clauses, and a separate diluent, and instructions for use, including an instruction for reconstituting the solid unit dose using the diluent to prepare a liquid composition capable of being inhaled by the host animal.

7. The kit of any one of the preceding clauses further comprising a container.

8. The method, composition, unit dose, or kit of any one of the preceding clauses wherein the composition is a dry powder adapted for inhalation by the host animal.

9. The method, composition, unit dose, or kit of any one of the preceding clauses wherein the composition is a solution adapted for aerosolization and inhalation by the host animal.

10. The method, composition, unit dose, or kit of any one of the preceding clauses wherein compound is delivered to achieve a lung concentration, such as measured in epithelial lining fluid (ELF), sputum, ling tissues, bronchial lavage fluid, and the like, of at least about 2 µg/mL, at least about 4 µg/mL, at least about 8 µg/mL or at least about 16 µg·mL 11. The method, composition, unit dose, or kit of any one of the preceding clauses wherein X and Y are taken together with the attached carbon to form carbonyl.

12. The method, composition, unit dose, or kit of any one of the preceding clauses wherein Z is a monosaccharide.

13. The method, composition, unit dose, or kit of any one of the preceding clauses wherein Z is desosamine or a derivative thereof.

14. The method, composition, unit dose, or kit of any one of the preceding clauses wherein Z is desosamine.

15. The method, composition, unit dose, or kit of any one of the preceding clauses wherein V is C(O).

16. The method, composition, unit dose, or kit of any one of the preceding clauses wherein W is H or F.

17. The method, composition, unit dose, or kit of any one of the preceding clauses wherein W is F.

18. The method, composition, unit dose, or kit of any one of the preceding clauses wherein A is CH$_2$.

19. The method, composition, unit dose, or kit of any one of the preceding clauses wherein B is (CH$_2$)$_n$.

20. The method, composition, unit dose, or kit of any one of the preceding clauses wherein n is an integer from 2 to 4

21. The method, composition, unit dose, or kit of any one of the preceding clauses wherein n is 3.

22. The method, composition, unit dose, or kit of any one of the preceding clauses wherein C is aryl, arylalkyl, heteroaryl, or heteroarylalkyl, each of which is optionally substituted.

23. The method, composition, unit dose, or kit of any one of the preceding clauses wherein C is aryl, arylalkyl, heteroaryl, or heteroarylalkyl, each of which is substituted.

24. The method, composition, unit dose, or kit of any one of the preceding clauses wherein C is aryl or heteroarylalkyl, each of which is optionally substituted.

25. The method, composition, unit dose, or kit of any one of the preceding clauses wherein C is optionally substituted aryl or substituted aryl.

26. The method, composition, unit dose, or kit of any one of the preceding clauses wherein C is aminophenyl.

27. The method, composition, unit dose, or kit of any one of the preceding clauses wherein C is 3-aminophenyl.

28. The method, composition, unit dose, or kit of any one of the preceding clauses wherein the compound is solithromycin, or a pharmaceutically acceptable salt, hydrate, solvate, or prodrug thereof 29. The method, composition, unit dose, or kit of any one of the preceding clauses wherein the compound is solithromycin, or a pharmaceutically acceptable salt thereof 30. The method, composition, unit dose, or kit of any one of the preceding clauses wherein the compound is solithromycin.

31. The method, composition, unit dose, or kit of any one of the preceding clauses wherein the administration is performed using a nebulizer, and the composition or unit dose is capable of producing a aerosol particle with an MMAD predominantly in the range from about 1 to about 5 μm.

32. The method, composition, unit dose, or kit of any one of the preceding clauses further comprising the step of administering a therapeutically effective amount of an aminoglycoside.

33. The method, composition, unit dose, or kit of any one of the preceding clauses wherein the aminoglycoside is selected from the group consisting of tobramycin, amikacin, and a combination thereof.

34. The method, composition, unit dose, or kit of any one of the preceding clauses wherein the compound is administered at a dose lower than that capable of antagonizing or significantly antagonizing the efficacy of the aminoglycoside.

35. The method, composition, unit dose, or kit of any one of the preceding clauses further comprising the step of administering a therapeutically effective amount of a fluoroquinolone antibiotic.

36. The method, composition, unit dose, or kit of any one of the preceding clauses wherein the fluoroquinolone is levofloxacin 37. The method, composition, unit dose, or kit of any one of the preceding clauses further comprising the step of administering a therapeutically effective amount of aztreonam.

38. The method, composition, unit dose, or kit of any one of the preceding clauses wherein the disease includes ventilator associated pneumonia (VAP), hospital acquired pneumonia (HAP), community acquired bacterial pneumonia (CABP), or a combination thereof.

39. The method, composition, unit dose, or kit of any one of the preceding clauses wherein the disease includes cystic fibrosis, lung cancer, obstructive lung diseases, such as chronic obstructive pulmonary disease, asthma, chronic bronchitis, restrictive lung diseases, emphysema, primary and secondary ciliary dyskinesia, sinusitis, pneumonia, mesothelioma, or a combination thereof.

40. The method, composition, unit dose, or kit of any one of the preceding clauses wherein the disease includes cystic fibrosis.

41. The method, composition, unit dose, or kit of any one of the preceding clauses wherein the host animal is immunocompromised.

41. The method, composition, unit dose, or kit of any one of the preceding clauses wherein the disease is caused at least in part by a gram-negative bacteria such as *Pseudomonas* spp., *Stenotrophomonas maltophilia, Burkholderia cepacia, Aeromonas hydrophilia, Escherichia coli, Citrobacter freundii, Salmonella* spp., *Shigella* spp., *Enterobacter* spp., *Klebsiella* spp., *Serratia marcescens, Francisella tularensis, Morganella morganii, Proteus* spp., *Providencia* spp., *Acinetobacter* spp., *Yersinia enterocolitica, Yersinia* spp., *Bordetella* spp., *Haemophilus* spp., *Pasteurella* spp., *Branhamella catarrhalis, Helicobacter pylori, Campylobacter* spp., *Borrelia* spp., *Legionella pneumophila, Listeria monocytogenes, Neisseria gonorrhoeae, Neisseria meningitidis, Kingella, Moraxella, Gardnerella vaginalis, Bacteroides* spp., and the like.

42. The method, composition, unit dose, or kit of any one of the preceding clauses wherein the disease is caused at least in part by a gram-positive bacteria such as *Corynebacterium* spp., *Streptococcus* spp., *Enterococcus* spp., *Staphylococcus* spp., and the like.

43. The method, composition, unit dose, or kit of any one of the preceding clauses wherein the disease is caused at least in part by a gram-positive anaerobic bacteria such as *Clostridium* spp.

44. The method, composition, unit dose, or kit of any one of the preceding clauses wherein the disease is caused at least in part by an acid-fast bacteria such as *Mycobacterium tuberculosis, Mycobacterium avium, Mycobacterium intracellulare*, and *Mycobacterium leprae*.

45. The method, composition, unit dose, or kit of any one of the preceding clauses wherein the disease is caused at least in part by an atypical bacteria such as *Chlamydia pneumoniae* and *Mycoplasma pneumoniae*.

46. The method, composition, unit dose, or kit of any one of the preceding clauses wherein the disease is caused at least in part by one or more strains of *Pseudomonas aeruginosa*, mucoid *Pseudomonas aeruginosa, Burkholderia cepacia, Staphylococcus aureus*, including MRSA, or a combination thereof.

47. The method, composition, unit dose, or kit of any one of the preceding clauses wherein the disease is caused at least in part by one or more CF strains of *Pseudomonas aeruginosa*, mucoid *Pseudomonas aeruginosa, Burkholderia cepacia, S. aureus*, including MRSA, or a combination thereof.

48. The method, composition, unit dose, or kit of any one of the preceding clauses wherein the mucoid *Pseudomonas aeruginosa* is pyocyanin positive.

49. The method, composition, unit dose, or kit of any one of the preceding clauses wherein the disease is caused at least in part by one or more strains of *Staphylococcus aureus*, including susceptible and resistant strains, such as MRSA, *B. anthracis*, or a combination thereof.

50. The method, composition, unit dose, or kit of any one of the preceding clauses wherein the disease is caused at least in part by one or more strains of MRSA.

51. The method, composition, unit dose, or kit of any one of the preceding clauses wherein the disease is caused at least in part by one or more of clarithromycin resistant bacteria, including multi-resistance or pan-resistance, or a combination thereof.

52. The method, composition, unit dose, or kit of any one of the preceding clauses wherein the disease is caused at least in part by inflammation.

53. The method, composition, unit dose, or kit of any one of the preceding clauses wherein the disease is caused at least in part by inflammation arising from TNFα production, CXCL8 production, IL-8 production, MMP9 production, or a combination thereof.

54. The method, composition, unit dose, or kit of any one of the preceding clauses wherein the host animal is a mammal.

55. The method, composition, unit dose, or kit of any one of the preceding clauses wherein the host animal is a human.

Illustrative inhalable compounds, compositions, and formulations include inhalable dry powders and inhalable aerosolizable solutions. It is to understood that the inhalable compounds, compositions, and formulations may provide additional benefits due to the direct delivery to the endobronchial site of infection, such as decreased toxicity compared to other systemic delivery, reduced cost, and better patient compliance, such as compared to IV antibiotic administration requiring an inpatient or outpatient visit.

Illustrative inhalable compounds, compositions, and formulations are adapted for delivery to the lungs and endobronchial space of the patient, such as by aerosolization or dry powder inhalation. Such compounds may be lyophilizates, or reconstitutable lypophilizates, as described in PCT International Publication No. WO 2011/112864, the disclosure of which is incorporated herein by reference. In another embodiment, the compounds are prepared as liposomes, including charged liposomes and antibody coated liposomes, nanoparticulate or microparticulate compositions, nanosuspensions, and the like. The inhalable compounds, compositions, and formulations may include one or more pharmaceutically acceptable carriers, excipients, suspending agents, diluents, fillers, salts, buffers, stabilizers, solubilizers, solvents, dispersion media, coatings, isotonic agents, and other materials. The inhalable compounds, compositions, and formulations may include potentiators, complexing agents, targeting agents, stabilizing agents, cosolvents, pressurized gases, or solubilizing conjugates.

Illustrative excipients include sugars such as lactose, sucrose, mannitol, or sorbitol; cellulose preparations such as, maize starch, wheat starch, rice starch, potato starch, gelatin, gum tragacanth, methyl cellulose, hydroxypropylmethylcellulose, sodium caroxymethylcellulose, and/or polyvinylpyrrolidone (PVP). Preferred excipients include lactose, gelatin, sodium carboxymethyl cellulose, and low molecular weight starch products.

Illustrative suspending agents that can serve as valve lubricants in pressurized pack inhaler systems include oleic acid, simple carboxylic acid derivatives, and sorbitan trioleate.

Illustrative diluents include water, saline, phosphate-buffered citrate or saline solution, and mucolytic preparations. Other illustrative diluents include alcohol, propylene glycol, and ethanol. Other illustrative diluents have a tonicity and pH compatible with the alveolar apparatus. Other illustrative diluents include isotonic saline, phosphate buffered isotonic solutions whose tonicity have been adjusted with sodium chloride or sucrose or dextrose or mannitol.

Illustrative fillers include glycerin, propylene glycol, ethanol in liquid or fluid preparations. Illustrative fillers for dry powder inhalation systems include lactose, sucrose, dextrose, suitable amino acids, and derivatives of lactose. In another embodiment, the fillers include glycerin, propylene glycol, lactose and amino acids.

Illustrative salts include those that are physiologically compatible and provide the desired tonicity adjustment, including monovalent and divalent salts of strong or weak acids. In another embodiment, the salts include tartrates.

Illustrative buffers include phosphate or citrate buffers or mixed buffer systems of low buffering capacity. In another embodiment, the buffers include phosphate.

Illustrative coating agents to provide a hydrophobic sheath around the hydrophilic cores include caproic and lauric acids. During the preparation of liposomes the use of diphosphatidyl choline or diphosphatidyl myristyl choline or suitable such mixtures can be used to provide protection to the molecules or formulation.

Illustrative stabilizers include those that provide chemical or physical stability of the final preparations. Such stabilizers include antioxidants such a sodium metabisulfite, alcohol, polyethylene glycols, butylated hydroxyanisole, butylated hydroxytoluene, disodium edetate. In another embodiment, the stabilizers include sodium metabisulfite, disodium edetate and polyethylene glycols. In another embodiment, the stabilizers include cryoprotectants such as polyethylene glycols, sugars, and carrageenans.

Illustrative solubilizers include propylene glycol, glycerin, suitable amino acids, complexing agents such as cyclodextrins, sorbitol solution, or alcohol. In another embodiment, the solubilizers include ethanol, propylene glycol, glycerin, sorbitol, and cyclodetrins. In another embodiment, the solubilizers include propylene glycol, sorbitol, and cyclodextrins.

It is to be understood that the formulations described herein may include any and all selections from the above lists of components, in any combination.

In another embodiment, the active ingredients are formulated for inhalation with use of a suitable propellant such as dichlorodifluoromethane, dichloroflouromethane, dichlorotetrafluoroethane, carbon dioxide or other gas. In another embodiment, the propellants include non-CFC related class of propellants or related analogs.

In another embodiment, the active ingredients are dried into an inhalable dry powder by mixing with suitable adjuvants that are compatible with the compounds described herein and are biologically compatible. Illustrative methods of drying the pharmaceutical material for inhalation include spray drying, conventional bed drying, and/or super critical fluid processing. In another embodiment, spray drying and super critical fluid processing are used.

In another embodiment, the compounds, compositions, and formulations are adapted for aerosolization as concentrated solutions of the compounds, such as about 1 to about 5 mL solutions of about 100 to about 1,000 mg, about 200 to about 800 mg, about 400 to about 600 mg, about 400 to about 500 mg, about 200 to about 400 mg, about 200 to about 300 mg, about 100 to about 400 mg, about 100 to about 300 mg, or about 100 to about 200 mg of the compounds.

Illustrative diseases treatable with the compounds, compositions, formulations, and methods described herein include cystic fibrosis (CF), ventilator associated pneumonia (VAP), hospital acquired pneumonia (HAP), community acquired bacterial pneumonia (CABP), and combinations thereof.

Illustrative diseases treatable with the compounds, compositions, formulations, and methods described herein also include lung cancer, obstructive lung diseases, such as chronic obstructive pulmonary disease, asthma, chronic bronchitis, restrictive lung diseases, emphysema, primary and secondary ciliary dyskinesia, sinusitis, pneumonia, mesothelioma, and combinations thereof.

In another embodiment, compounds, compositions, formulations, and methods are described herein for treating cystic fibrosis. In another embodiment, compounds, compositions, formulations, and methods are described herein for treating immunocompromised patients having a bacterial infection.

Illustrative diseases treatable with the compounds, compositions, formulations, and methods described herein include diseases caused at least in part by one or more strains of *Pseudomonas aeruginosa*, mucoid *Pseudomonas aeruginosa, Burkholderia cepacia, Staphylococcus aureus*, including MRSA, or a combination thereof.

Illustrative diseases treatable with the compounds, compositions, formulations, and methods described herein include diseases caused at least in part by one or more CF strains of *Pseudomonas aeruginosa*, mucoid *Pseudomonas aeruginosa, Burkholderia cepacia, S. aureus*, including MRSA, or a combination thereof. In one variation, the mucoid *Pseudomonas aeruginosa* is pyocyanin positive.

Illustrative diseases treatable with the compounds, compositions, formulations, and methods described herein include diseases caused at least in part by one or more strains of *Staphylococcus aureus*, including susceptible and resistant strains, such as MRSA, *B. anthracis*, or a combination thereof Illustrative diseases treatable with the compounds, compositions, formulations, and methods described herein include diseases caused at least in part by one or more strains of MRSA.

Illustrative diseases treatable with the compounds, compositions, formulations, and methods described herein include diseases caused at least in part by one or more of clarithromycin resistant bacteria, including multi-resistance and pan-resistance.

It has been reported that cystic fibrosis patients and other patients with chronic endobronchial infections may have a high incidence of bronchospastic or asthmatic airways. These airways are sensitive to hypotonic or hypertonic aerosols, to the presence of a permanent ion, particularly a halide such as chloride, as well as to aerosols that are acidic or basic. The effects of irritating the airways can be clinically manifested by cough or bronchospasm. It is therefore appreciated that the formulations described herein desirably have adjusted osmolality, tonicity, ionic strength and pH.

In another embodiment, the aerosolizable formulations have salinity adjusted to be well-tolerated by patients. In another embodiment, formulation has balanced osmolality ionic strength and chloride concentration. In another embodiment, the formulation has the smallest reasonable aerosolizable volume able to deliver the effective dose of the compounds to the site of the infection. In another embodiment, the formulation does not negatively impair airway function and does not cause any undesirable side effects.

In another embodiment, the aerosolizable solution formulations are physiologically acceptable solutions, such as saline and/or buffered saline solutions. Illustrative saline concentrations are physiological, such as about 0.9% saline, or sub-physiological, such as in the range from about 0.1% saline to less than about 0.9% saline, including about 0.225% saline (25% physiological saline) solutions. It is to be understood that the formulations may also contain bromide and/or iodide. In another embodiment, the pH of the solutions are in the range from about 4.2 to about 7.5, about 4.5 to about 7.5, about 4.5 to about 7, about 5.5 to about 7, or about 5.5 to about 6.5, or at about 6.0. It is to be understood that the foregoing pHs may be buffered or unbuffered.

In another embodiment, the aerosolizable formulations are dry powders or liquids formed from or capable of forming small particles suitable for deep endobronchial entry, such as small particles having average diameter, such as a mass medium average diameter (MMAD) predominantly of about 10 μm or less, such as in the range of about 1 to about 10 μm; predominantly of about 5 μm or less, such as in the range from about 1 to about 5 μm, or in the range from about 2 to about 5 μm. In another embodiment, the formulations are capable of being aerosolized, such as by nebulization, and/or are capable of forming small particles suitable for deep endobronchial entry, such as having average diameter, such as a MMAD predominantly of about 5 μm or less, such as in the range from about 1 to about 5 μm. As used herein, predominantly or a majority of generally refers to about 70% or greater, about 80% or greater, or about 90% or greater of the particles are about 10 μm or less, such as in the range of about 1 to about 10 μm; or about 5 μm or less, such as in the range from about 1 to about 5 μm, or in the range from about 2 to about 5 μm. It is to be understood that standard deviations of less than or equal to about 3 μm, or less than or equal to about 2 μm are observed in the foregoing ranges. It is to be understood that the foregoing specifically describes each and all integral values in each range.

In another embodiment, the aerosolizable solution formulations have an osmolarity in the range from about 50 to about 1050 mOsm/L, or in the range from about 50 to about 550 mOsm/L, or in the range from about 100 to about 750 mOsm/L, or in the range from about 200 to about 750 mOsm/L, or in the range from about 200 to about 600 mOsm/L, or in the range from about 300 to about 600 mOsm/L, or in the range from about 300 to about 500 mOsm/L, or in the range from about 150 to about 250 mOsm/L, or in the range from about 165 to about 190 mOsm/L. In another embodiment, the formulations have an osmolality in the range from about 50 to about 550 mOsm/kg, or in the range from about 165 to about 190 mOsm/kg.

In another embodiment, the compounds described herein are administered as an aerosol suspension, such as an aerosol suspension of liposomes or other microscopic particles.

In another embodiment, the aerosol formulation is nebulized into particle sizes which can be delivered to all parts of the lung, throughout the endothelial tree including the bronchi and bronchioli and the terminal and respiratory bronchioles, and the alveoli, where the bacteria may be present. It is appreciated that *Pseudomonas aeruginosa* bacterium or other susceptible bacteria that reside in patients with cystic fibrosis may be located in the terminal and respiratory bronchioles. It is further appreciated that during exacerbation of infection, bacteria can also be present in alveoli.

In another embodiment, the formulation or composition is a dry powder comprising a compound described herein. In one aspect, the dry powder is dispersed into an inhalable configuration that comprises or consists essentially of particles having a MMAD of about 5 μm or less, or in the range from about 1 to about 5 μm, or in the range from about 2 to about 5 μm, or in the range from about 3 to about 5 μm.

Dry powder formulations may be prepared using any conventional process, including but not limited to milling, including media milling, jet milling, and the like, lyophilizing, spray drying, precipitating into a fine powder, and the like.

Illustratively, spray drying is accomplished by suspending the compounds described herein in water, stirring and cooling. The solution is optionally purified using a charcoal and filtered. Subsequently, the solution is spray dried using any suitable spay-drying equipment, such as, for example Buchi Mini Spray Dryer B-191.

Particle size determinations may be made using a multi-stage cascade impactor or other suitable method. Illustratively, the Thermo Andersen Eight Stage Non-Viable Cascade Impactor is specifically cited within the US Pharmacopoeia Chapter 601 as a characterizing device for aerosols within metered-dose and dry powder inhalers. The Eight Stage Cascade Impactor utilizes eight jet stages enabling classification of aerosols from 9.0 micrometers to 0.4 micrometers (at 28.3 L/min) and allows airborne particulate to impact upon stainless steel impaction surfaces or a variety of filtration media substrates. A final filter collects all particles smaller than 0.4.

Illustratively, media milling is accomplished by placing the compounds described herein into a mill containing, for example, stainless steel or ceramic balls and rotating or tumbling the material until the desired drug particle size ranges are achieved. It is appreciated that the advantages of media milling may include good size control, narrow product size ranges, high efficiencies of recovery, and readily scalable processes.

Illustratively, jet milling uses very high pressure air streams to collide particles with one another, with fine particles of the desired size being recovered from the mill. It is appreciated that the advantages of jet milling may include rapidity of the manufacturing process and less energy transfer during milling, resulting in less temperature rise during the drug production. The jet milling process is generally completed in seconds to minutes.

Illustratively, precipitation and/or crystallization is accomplished by adding a co-solvent to a solution of one or more compounds described herein that decreases the solubility of compounds to a uniform drug solution results in solute precipitation and/or crystallization. When sufficient co-solvent is added, the solubility of the compounds fall to the point where solid drug particles are formed which can be collected by filtration or centrifugation. It is appreciated that precipitation and/or crystallization may have the advantage of being highly reproducible, having a high yield of recovery and being able to be performed under low temperature conditions, which reduce degradation.

In another embodiment, the nebulization rate of the aerosolizable formulations is at least about 1 µL/sec, at least about 2 µL/sec, at least about 3 µL/sec, at least about 4 μL/sec, or at least about 5 μL/sec In another embodiment, the delivered unit dose is about 5 mL, about 4.5 mL, about 4 mL, about 3.75 mL, or about 3.5 mL. It is to be understood that the packaging may include more material, but it is configured so that the delivered dose is a predetermined portion thereof.

Illustrative nebulizers capable of providing aerosols of the formulations described herein include atomizing, jet, electronic, and ultrasonic nebulizers, pressurized, vibrating porous plate or equivalent nebulizers or by dry powder inhalers which predominantly produce aerosols or dry powder particles between 1 and 5 μm. It is appreciated that such particle sizes are desirable for efficacious delivery of compounds described herein into the endobronchial space to treat bacterial infections. The compositions and formulations are delivered by aerosolization using a nebulizer capable of producing a particle, where the majority of the particles have an average diameter of about 5 μm or less, or in the range from about 1 to about 5 μm.

Illustrative nebulizers include dry powder inhalers, metered dose inhalers, micronebulizers, ultrasonic nebulizers, and jet nebulizers, including standard and breath-enhanced (ultrasonic nebulizer (Ultraneb 100/99; Sunrise Medical HHG; Somerset, Pa.) specific nebulizer (Pari LC Plus Jet Nebulizer; Pari; Midlothian, Va.) and compressor (Pulmo-Aide; Sunrise Medical HHG).

Illustrative jet nebulizers, including breath enhanced jet nebulizers, are SIDESTREAM, PARI LC, PARI LC PLUS (Pari Respiratory Equipment, Richmond, Va.), and the like.

Illustrative ultrasonic nebulizers include AEROSONIC (from DeVilbiss), ULTRAAIRE (from Omron), and the like.

In another embodiment, the formulation is administered on a daily dosing schedule, including but not limited to q.d., b.i.d., t.i.d., q 8h, and the like. In one embodiment, the daily dosing schedule is 1 to 4 times daily, t.i.d., q 8h, or b.i.d. In another embodiment, the daily dosing schedule is t.i.d. during awake hours, such as t.i.d. at 7 hour intervals or t.i.d. at 6 hour intervals.

In another embodiment, the compounds described herein are co-administered with an aminoglycoside, where the compounds described herein are dosed in the alternative of the aminoglycoside, such as during the 28 day mandatory off period for tobramycin dosing per manufacturer labeling required to prevent permanent tobramycin resistance.

In another embodiment, the formulation is contained in a five-milliliter plastic vial, such as low-density polyethylene (LDPE) vial. The vials may be aseptically filled using a blow-fill-seal process. Additional alternative illustrative packages are described in U.S. Pat. Nos. 5,409,125, 5,379,898, 5,213,860, 5,046,627, 4,995,519, 4,979,630, 4,951,822, 4,502,616 and 3,993,223, the disclosures of which are incorporated herein by this reference. The unit dose containers may be designed to be inserted directly into a particular device adapted to allow inhalation of the compound. Illustratively, the vials are sealed in foil over-pouches, six per over-pouch.

Illustrative parenteral doses of the macrolides are described in U.S. Patent Application Ser. No. 61/312,417, the disclosure of which is incorporated herein by reference.

In another embodiment, the macrolides described herein are co-administered with one or more other antibiotics, such as one or more other aminoglycosides, one or more other fluoroquinolones, aztreonam, and/or fosfomycin. In one variation, such co-administration may be performed without antagonism of the action of the aminoglycosides. In one aspect, the macrolides are administered at a dose lower than that capable of antagonizing or significantly antagonizing the efficacy of the aminoglycoside. In another variation, such co-administration may be performed to synergize the activity of another antibiotic, such as an aminoglycoside, a fluoroquinolone, aztreonam, and/or fosfomycin.

Antibiotic aminoglycosides, such as tobramycin, have been an important addition to the available therapies for treating pseudomonal infections. *Pseudomonas aeruginosa* grows in the endobronchial space and is found in the sputum of patients suffering from or in need of relief from pathogenic bacterial infections. During exacerbations of infection, *Pseudomonas aeruginosa* growth may also occur in the alveoli of patients. Illustrative diseases caused by pathogenic endobronchial *Pseudomonas aeruginosa* include cystic fibrosis.

In another illustrative embodiment, methods for treating cystic fibrosis (CF) are described herein. In one aspect, the methods include the step of administering one or more macrolides described herein. In one variation, the methods also include the step of administering one or more aminoglycosides. In another variation, the methods also include the step of administering one or more fluoroquinolones. In another variation, the methods also include the step of administering aztreonam. In another variation, the methods also include the step of administering fosfomycin. In one variation of any of the foregoing methods, the method includes the step of administering the fluoroquinolones, such as levofloxacin, aminoglycoside antibiotics, such as tobramycin, aztreonam, and/or fosfomycin by inhalation.

Illustrative aminoglycosides include, but are not limited to, amikacin, apramycin, arbekacin, astromicin, bekanamycin, dibekacin, framycetin, gentamicin, hygromycin B, isepamicin, kanamycin, neomycin, netilmicin, paromomycin, paromomycin sulfate, rhodostreptomycin, ribostamycin, sisomicin, spectinomycin, streptomycin, tobramycin, verdamicin, and combinations thereof.

In another embodiment, the aminoglycoside is selected from gentamycin, amikacin, kanamycin, streptomycin, neomycin, netilmicin and tobramycin, and combinations thereof.

Illustrative dosing regimens and protocols for aminoglycoside antibiotics that may be used in the methods described herein, are described in U.S. Pat. Nos. 5,508,269, 6,083,922, and 6,890,907, the disclosures of which are incorporated herein by reference. In one variation, the method includes the step of administering the aminoglycoside antibiotic, such as tobramycin, by inhalation.

Any conventional dosage unit, formulation, and/or method of administering aminoglycosides may be used herein, such as the dosage units, formulations, and/or methods of administering tobramycin as described in U.S. Pat. Nos. 5,508,269, 6,890,907, 6,083,922, and 7,696,178, the disclosures of which are incorporated herein by reference.

Illustrative fluoroquinolone antibiotics include, but are not limited to oxolinic acid (Uroxin), piromidic acid (Panacid), pipemidic acid (Dolcol), rosoxacin (Eradacil), ciprofloxacin (Ciprobay, Cipro, Ciproxin), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), levofloxacin (Cravit, Levaquin), moxifloxacin (Avelox, Vigamox, pazufloxacin (Pasil, Pazucross), sparfloxacin (Zagam), tosufloxacin (Ozex, Tosacin), clinafloxacin, gemifloxacin (Factive), sitafloxacin (Gracevit), prulifloxacin (Quisnon), delafloxacin, and combinations thereof.

Any conventional dosage unit, formulation, and/or method of administering fluoroquinolone antibiotics may be used herein.

Any conventional dose, formulation, and/or method of administering aztreonam may be used herein, such as the dosage units, formulations, and/or methods of administering aztreonam as described in U.S. Pat. Nos. 6,660,249 and 7,214,364, the disclosures of which are incorporated herein by reference.

In another embodiment, one or more macrolides described herein are administered in a suppression therapy protocol. In another embodiment, one or more macrolides described herein are administered in an adjunct therapy protocol for an acute exacerbation of the pulmonary disease, such as CF. In another embodiment, the protocol is capable of preventing or delaying chronic *P. aeruginosa* infection and/or colonization.

In another embodiment, one or more macrolides described herein, such as CEM-101, are co-administered with tobramycin.

In another embodiment, one or more macrolides described herein, such as CEM-101, are co-administered with levofloxacin.

In another embodiment, one or more macrolides described herein, such as CEM-101, are co-administered with aztreonam.

In another embodiment, CEM-101 is co-administered with tobramycin, where the CEM-101 is administered orally and the tobramycin is administered by inhalation. In another embodiment, CEM-101 is co-administered with aztreonam, where the CEM-101 is administered orally and the aztreonam is administered by inhalation. In another embodiment, CEM-101 is co-administered with tobramycin, where the CEM-101 is administered by inhalation and the tobramycin is administered by inhalation. In another embodiment, CEM-101 is co-administered with aztreonam, where the CEM-101 is administered by inhalation and the aztreonam is administered by inhalation. In one variation, the co-administration follows a protocol where the tobramycin or a aztreonam is administered during a first period of administration, for example days 1-28, and the CEM-101 is administered during a second period, for example days 29-56. The alternate periods may be repeated.

In another embodiment, illustrative daily oral doses of the macrolides described herein, such as CEM-101, are in the range from about 1 to about 25 mg/kg, about 1 to about 10 mg/kg, about 2 to about 8 mg/kg, or about 4 to about 6 mg/kg of patient body weight. In another embodiment, illustrative daily adult human oral doses of the macrolides described herein, such as CEM-101, are in the range from about 100 to about 1,000 mg, about 200 to about 800 mg, or about 400 to about 600 mg. In another embodiment, the daily dose is single or divided and may be administered qd, bid, tid, and the like.

It is understood that dosing is desirably performed to achieve sputum concentrations at least about 10 times the MIC for one or more of the target organisms of the infection or disease. Without being bound by theory, it is believed that such illustrative dosages are sufficient to achieve lung levels of about 1 µg/mL or greater, about 2 µg/mL or greater, about 4 µg/mL or greater, or about 8 µg/mL or greater, which may in most cases correspond to a concentration that is about 10 times the MIC or greater. Without being bound by theory, it is also believed that such illustrative dosages be sufficient to observe bactericidal activity against lung pathogens.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

As used herein, the term therapeutically effective amount as applied to compositions, formulation, kits, methods, and the like, illustratively may include an amount that achieves sputum concentration of the compounds at about 10× the MIC or greater for the target organism.

It is appreciated that successful therapy may be monitored by any conventional method or endpoint, including but not limited to the decrease in the decline of or the improvement in forced expiratory volume (FEV), and/or forced vital capacity (FCV). It is further appreciated that successful therapy may be monitored by the decrease or the decrease in the growth of colony forming units (CFUs) of the target bacteria in sputum. It is further appreciated that successful therapy may be monitored by a decrease in persisters of *Pseudomonas* and/or *Burkholderia* species.

Illustrative target pathogenic bacteria include, but are not limited to, staphylococci, including coagulase-negative staphylococci and coagulase-positive staphylococci, streptococci, including Group A beta hemolytic streptococci, non-Group A beta hemolytic streptococci and viridans group streptococci, enterococci, *Nesseria* species, *Clostridium* species, *Bordetella* species, *Bacillus* species and *Corynebacterium* species. In particular, the bacterial infection is an infection caused by bacteria selected from the group consisting of *Staphylococcus aureus* (methicillin-resistant and -susceptible), *Staphylococcus epidermidis, Staphylococcus hemolyticus, Staphylococcus saprophyticus, Staphylococcus lugdunensis, Staphylococcus capitis, Staphylococcus caprae, Staphylococcus saccharolyticus, Staphylococcus simulans, Staphylococcus warneri, Staphylococcus hominis, Staphylococcus intermedius, Staphylococcus pseudointermedius, Staphylococcus lyricus, Streptococcus pyogenes, Streptococcus agalactiae, Streptococcus dysgalactiae* subspecies *dysgalactiae, Streptococcus anginosus, Streptococcus mitis, Streptococcus salivarius, Streptococcus bovis, Streptococcus mutans, Pseudomonas aeruginosa, Neisseria gonorrhoeae, Neisseria meningitidis, Bacillus anthracis, Bordetella pertussis, Burkholderia cepacia, Clostridium difficile, Enterococcus faecalis, Enterococcus faecium* and *Corynebacterium diphtheriae*. In particular aspects, the bacterial infection is an infection caused by *Staphylococcus aureus* (methicillin-resistant or -susceptible In another illustrative embodiment, the macrolides described herein are of the formula

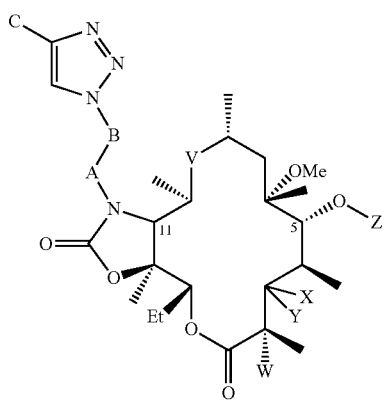

and pharmaceutically acceptable salts, hydrates, solvates, esters, and prodrugs thereof, wherein:

X is H; and Y is $OR_7$; where $R_7$ is a monosaccharide or disaccharide, or a derivative thereof; or X and Y are taken together with the attached carbon to form carbonyl;

Z is a monosaccharide or disaccharide, or a derivative thereof;

V is C(O), or $C(=NR_{11})$, wherein $R_{11}$ is hydroxy or alkoxy;

W is H, F, Cl, Br, I, or OH;

A is $CH_2$, C(O), C(O)O, C(O)NH, $S(O)_2$, $S(O)_2NH$, or $C(O)NHS(O)_2$;

B is $(CH_2)_n$ where n is an integer in the range from 0 to about 10, or B is $C_2$-$C_{10}$ alkenyl or alkynyl; and C is cycloalkyl, cycloheteroalkyl, aryl, arylalkyl, heteroaryl, or heteroarylalkyl, each of which is optionally substituted.

In another embodiment, X and Y are taken together with the attached carbon to form carbonyl. In another embodiment, Z is a monosaccharide or a derivative thereof. In another embodiment, Z is an amino-containing monosaccharide, such as an amino glucose or a derivative, analog, or stereoisomer thereof, including but not limited to desosamines and derivatives thereof, mycaminose and derivatives thereof, vancosamine and derivatives thereof, L-vancosamine, 3-desmethyl-vancosamine, 3-epi-vancosamine, 4-epi-vancosamine, acosamine, 3-amino-glucose, 4-deoxy-3-amino-glucose, actinosamine, daunosamine, 3-epi-daunosamine, ristosamine, N-methyl-D-glucamine, and the like. In another embodiment, Z is a desosamine or a derivative thereof. In another embodiment, Z is a mycaminose or a derivative thereof. In another embodiment, Z is a desosamine. In another embodiment, Z is a mycaminose. In another embodiment, V is C(O). In another embodiment, W is H or F. In another embodiment, W is F. In another embodiment, A is $CH_2$. In another embodiment, B is $(CH_2)_n$ where n is an integer in the range from about 2 to about 4. In another embodiment, B is $(CH_2)_3$. In another embodiment, C is optionally substituted aryl. In another embodiment, C is amino substituted aryl.

It is to be understood that each of the foregoing selections of X, Y, Z, W, A, B, and n may be combined without limitation, and therefore, such subgenera of compounds are specifically described herein. For example, in another embodiment, X and Y are taken together with the attached carbon to form carbonyl, and Z is a monosaccharide or a derivative thereof; or X and Y are taken together with the attached carbon to form carbonyl, and V is C(O); or X and Y are taken together with the attached carbon to form carbonyl, W is F, and A is $CH_2$; or Z is a desosamine or a derivative thereof, V is C(O), A is $CH_2$, and B is $(CH_2)_n$ where n is an integer in the range from about 2 to about 4; and the like.

In another embodiment, the macrolide described herein is of the formula

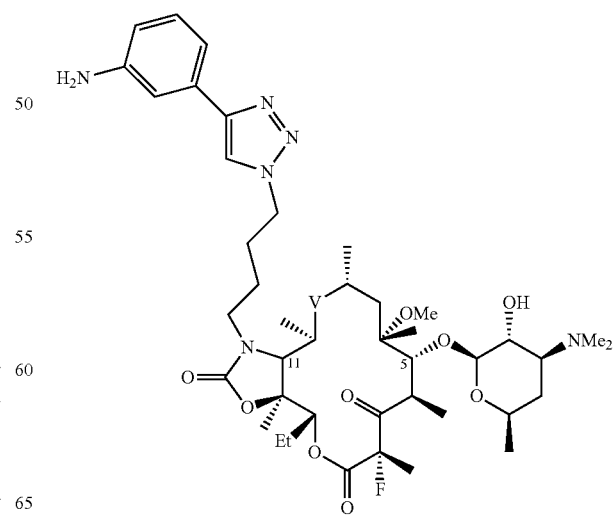

also known as CEM-101 or solithromycin, or a pharmaceutically acceptable salt, hydrate, solvate, ester, or prodrug thereof.

The macrolides described herein may be prepared as described herein, or according to US Patent Application Publication No. 2006/0100164 and in PCT International Publication No. WO 2009/055557, the disclosures of which are incorporated herein by reference in their entirety.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl" includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical $—(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl) alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl, such as the aryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration. Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

EXAMPLES

Example. Inhalable Formulation

The compounds described herein, such as CEM-101, are formulated in conventional dry powder or solution formulations. The compounds may be optionally formulated as pharmaceutically acceptable salts. The dry powder formulations are administered using a passive dry powder inhaler. The solution formulations are administered using a pressured metered dose inhaler, a nebulizer, or similar device. Illustrative dry powder formulations include, but are not limited to, Pulmosphere (PS) formulations (Inhale Therapeutic Systems, San Carlos, Calif.), and the like. PS formulations are prepared according to Dellamary et al., Hollow porous particles in metered dose inhalers, Pharm Res 17:168-174 (2000). The disclosure of the foregoing publication, and each additional publication cited herein, are each incorporated herein by reference.

Example. Preparation of Pseudomonal Alginate

*P. aeruginosa*, such as NH57388A, is cultured in 50 mL Mueller-hinton broth (MHB) for 24 to 28 h at 37° C. with shaking (170 rpm). The bacterial cells are harvested by centrifugation (23,000×g, 30 min, 4° C.) and resuspended in 3 to 6 mL of MHB. The supernatant is collected and placed in an 80° C. water bath for 30 min. Alginate is precipitated by adding the supernatant to 150 mL of ice-cold 99% ethanol. The precipitated alginate is collected with a sterile bacterial loop and washed several times in sterile saline. The purified alginate is then resuspended in 10 mL of sterile saline and stirred vigorously to form a homogeneous suspension. The alginate concentration is measured and adjusted to a concentration of 2 to 3 mg/mL.

Example. Model of Acute Mouse Lung Infection

*P. aeruginosa*, such as ATCC 27853, is grown overnight in MHB at 35° C. The bacterial suspensions re adjusted to ca. $1 \times 10^5$ to $6 \times 10^5$ CFU/mL by correlation of the absorbance at 600 nm with predetermined plate counts. Female Swiss mice are made neutropenic by the i.p. injection of 150 mg/kg cyclophosphamide (Baxter, Deerfield, Ill.) on days 1 and 3. On day 4, the mice are infected by the intratracheal instillation of 0.05 mL of inoculum with a curved oral gavage tip attached to a 1-mL syringe. Antibiotic treatments are started at 24 h postinfection and are administered once or twice daily (BID) for 24 or 48 h. Antibiotics are aerosolized with a microspray aerosol device. All infections and aerosol treatments are performed while the mice are under isoflurane anesthesia (5% isoflurane in oxygen running at 4 L/min). An untreated group of mice (n=8) is killed prior to the initiation of treatment to determine baseline bacterial counts. At 12 to 16 h following administration of the last antibiotic dose, the treated animals (n=8) are killed by carbon dioxide asphyxiation. The lungs are removed aseptically and homogenized (Pro200 homogenizer; Pro Scientific, Monroe, Conn.) in 1 mL of sterile saline. Serial 10-fold dilutions of the homogenized lung are plated on Mueller-Hinton agar, and the colonies are counted. For the survival studies, mice (n=10) are observed for 7 days after the end of treatment or for a total of 9 days postinfection.

Example. Model of Chronic Mouse Lung Infection

*P. aeruginosa*, such as NH57388A, is cultured in 50 mL MHB for 24 to 28 h at 37° C. with shaking (170 rpm). The bacterial cells are harvested by centrifugation (23,000×g, 30 min, 4° C.) and resuspended in 3 to 6 mL of MHB. The bacterial suspension is diluted (1:10) in the alginate suspension to yield about $10^8$ CFU/mL. The initial establishment of infection is achieved by the establishment of a transient neutropenia by administration of a single 150-mg/kg i.p. dose of cyclophosphamide 4 days prior to infection. On day 4, the mice are infected by use of a curved bead-tipped oral gavage attached to a 1-mL syringe while the mice are under isoflurane anesthesia. Antibiotic treatments are started at 24 h postinfection and are administered BID for three consecutive days. Various concentrations of antibiotics are used, and they are administered either by an oral, i.p., or aerosol route with a microspray device. At 12 to 16 h following the last treatment, the mice are killed, and the colony counts in the lung are determined as described herein.

Statistical Analysis.

Survival and lung bacterial counts are analyzed by the log-rank test and the Mann-Whitney U test (GraphPad Prism, version 4.03), respectively. A P value of <0.05 is considered statistically significant.

Example

The compounds described herein are poor substrates of efflux pumps expressed in *P. aeruginosa* (PA). MICs of 36 clinical and laboratory strains of PA with known efflux phenotype are measured by microdilution in cation-adjusted Muller-Hinton broth (CA-MHB) or in RPMI medium (commonly used in eukaryotic cell culture). Phe-Arg-β-naphthylamide (PaβN, 50 mg/L) and EGTA 5 mM are used to inhibit efflux pumps and alter OM integrity, respectively. *P. aeruginosa* strain ATCC PAO1 is used as reference. PA12 is a clinical strain overexpressing the 4 main efflux systems (MexAB, MexCD, MexEF, MexXY), PA403 is a laboratory strain deleted in the genes coding for the 4 efflux systems. A series of reference strains or of clinical isolates for which the expression of genes coding for efflux pumps is known is also used for MICs determinations. MICs are measured by microdilution in MH broth or in RPMI medium (used for eukaryotic cells culture) supplemented with 10% of fetal calf serum, or in MH broth supplemented by increasing amounts of serum. EGTA (5 mM) was used as a chelating agent (disrupting outer membrane integrity) and PaβN (50 mg/L) as an unspecific efflux inhibitor. The results are shown in Table 1.

TABLE 1

| Strains | Efflux expression | ERY MHB | ERY RPMI | CLR MHB | CLR RPMI | AZM MHB | AZM RPMI | TEL MHB | TEL RPMI | CEM-101 MHB | CEM-101 RPMI |
|---|---|---|---|---|---|---|---|---|---|---|---|
| 12 | AB + CD + EF + XY+ | 512 | 32 | 512 | 16 | 256 | 2 | 128 | 4 | 128 | 4 |
| 434 | AB + CD + XY+ | 512 | 128 | 512 | 128 | 512 | 4 | 128 | 4 | 128 | 8 |
| 63 | AB + EF + XY+ | 512 | 64 | 512 | 32 | 256 | 2 | 128 | 4 | 64 | 4 |
| 207 | AB + EF + XY+ | 512 | 128 | 512 | 64 | 512 | 4 | 128 | 4 | 32 | 4 |
| 48 | CD + EF + XY+ | 512 | 64 | 512 | 64 | 256 | 2 | 128 | 8 | 128 | 4 |
| 49 | CD + EF + XY+ | 512 | 64 | 512 | 32 | 256 | 2 | 128 | 4 | 128 | 4 |
| 11 | AB + CD+ | 256 | 16 | 512 | 16 | 128 | 2 | 64 | 1 | 16 | 2 |
| 266B | AB + CD+ | 512 | 64 | 512 | 64 | 256 | 2 | 256 | 4 | 256 | 4 |
| 333A | AB + EF+ | 512 | 64 | 512 | 64 | 256 | 2 | 64 | 2 | 128 | 2 |
| 335 | AB + EF+ | 512 | 64 | 512 | 64 | 512 | 4 | 128 | 4 | 128 | 2 |
| 16 | AB + XY+ | 512 | 32 | 512 | 64 | 256 | 4 | 128 | 4 | 32 | 4 |
| 68 | AB + XY+ | 512 | 64 | 512 | 64 | 256 | 2 | 128 | 4 | 64 | 4 |
| 168B | CD + XY+ | 512 | 256 | 512 | 256 | 512 | 4 | 256 | 4 | 128 | 4 |
| 133 | EF + XY+ | 512 | 64 | 512 | 64 | 256 | 4 | 128 | 4 | 64 | 4 |
| 156 | EF + XY+ | 512 | 16 | 512 | 32 | 512 | 4 | 128 | 2 | 64 | 2 |
| 1 | AB+ | 512 | 8 | 512 | 32 | 128 | 4 | 128 | 4 | 128 | 2 |
| 21 | AB+ | 512 | 64 | 512 | 64 | 256 | 2 | 64 | 2 | 128 | 4 |
| 2 | CD+ | 512 | 256 | 512 | 128 | 512 | 4 | 256 | 16 | 256 | 8 |
| 41 | CD+ | 512 | 64 | 512 | 64 | 256 | 2 | 256 | 4 | 256 | 4 |
| 3 | EF+ | 256 | 8 | 256 | 16 | 64 | 2 | 64 | 0.25 | 8 | 1 |
| 40 | EF+ | 256 | 32 | 256 | 16 | 256 | 2 | 64 | 2 | 32 | 4 |
| 4 | XY+ | 512 | 32 | 512 | 32 | 256 | 2 | 128 | 4 | 128 | 4 |
| 22 | XY+ | 512 | 32 | 512 | 32 | 256 | 2 | 128 | 2 | 64 | 4 |
| PAO1 | REFERENCE | 512 | 32 | 512 | 32 | 256 | 4 | 256 | 2 | 128 | 4 |
| 397 | AB− | 16 | 2 | 16 | 2 | 8 | 1 | 8 | 0.03 | 2 | 1 |
| 392 | CD− | 256 | 16 | 256 | 16 | 128 | 2 | 32 | 0.5 | 16 | 1 |
| 398 | CD− | 16 | 4 | 32 | 4 | 16 | 1 | 8 | 0.25 | 4 | 2 |
| 391 | EF− | 256 | 32 | 256 | 16 | 128 | 2 | 64 | 2 | 32 | 2 |
| 394 | XY− | 512 | 32 | 512 | 32 | 256 | 4 | 64 | 1 | 32 | 4 |
| 400 | XY− | 16 | 4 | 16 | 4 | 8 | 2 | 8 | 0.25 | 4 | 1 |
| 395 | HI− | 256 | 32 | 256 | 32 | 128 | 2 | 32 | 2 | 64 | 2 |
| 396 | ompH− | 128 | 16 | 64 | 16 | 64 | 2 | 16 | 0.25 | 8 | 2 |
| 401 | ompH− | 8 | 4 | 8 | 2 | 8 | 2 | 4 | 1 | 2 | 2 |
| 399 | AB − EF− | 16 | 4 | 16 | 4 | 16 | 2 | 4 | 0.25 | 8 | 1 |
| 403 | AB − CD − EF − XY− | 16 | 4 | 16 | 4 | 8 | 2 | 4 | 0.5 | 4 | 1 |
| 405 | AB − CD − EF − XY− | 8 | 4 | 8 | 4 | 8 | 2 | 8 | 0.25 | 4 | 1 |

Table 2 shows the results obtained with PAO1 (wild-type), PA12 (overexpressing 4 efflux pumps), and PA403 (disrupted for genes coding for 5 efflux pumps).

significantly lower than levels found in lung or liver with levels 5 and 54-fold higher than plasma concentrations in rat and monkey, respectively.

TABLE 2

|  | PAO1 (a) | | | | | | PA12 (b) | | | | | |
|---|---|---|---|---|---|---|---|---|---|---|---|---|
|  | CA-MHB | | | RPMI | | | CA-MHB | | | RPMI | | |
|  | CT | PABN | EGTA | CT | PaBN | EGTA | CT | PaBN | EGTA | CT | PaBN | EGTA |
| ERY | 512 | 16 | 256 | 32 | 32 | 32 | 512 | 32 | 512 | 32 | 32 | 2 |
| CLR | 512 | 8 | 256 | 32 | 4 | 32 | 512 | 16 | 256 | 16 | 16 | 2 |
| AZI | 128 | 4 | 8 | 2 | 4 | 0.25 | 256 | 2 | 256 | 2 | 2 | 0.5 |
| TEL | 128 | 4 | 32 | 2 | 4 | 1 | 128 | 4 | 32 | 4 | 4 | 1 |
| CEM-101 | 32 | 8 | 8 | 2 | 2 | 1 | 32 | 4 | 16 | 4 | 4 | 1 |

|  | P403 © | | | | | |
|---|---|---|---|---|---|---|
|  | CA-MHB | | | RPMI | | |
|  | CT | PaBN | EGTA | CT | PaBN | EGTA |
| ERY | 16 | ND | 16 | 4 | 4 | 0.5 |
| CLR | 16 | ND | 32 | 4 | 4 | 0.5 |
| AZI | 8 | ND | 2 | 2 | 2 | 0.125 |
| TEL | 4 | ND | 2 | 0.5 | 1 | 0.06 |
| CEM-101d | 4 | ND | 1 | 1 | 2 | 0.25 |

MIC (mg/L) in control conditions (CT), in the presence of PaβN 50 mg/L or EGTA 5 mM.
(a) wild type strain;
(b) clinical isolate overexpressing MexAB-OprM, MexCD-OprI, MexEF-OprN, MexXY-OprM;
© Δ(MexAB-OprM), Δ(MexCD-OprJ), Δ(MexEF-OprN), Δ(MexJK), Δ(MexXY).

MICs of all molecules were high against PAO1 and PA12 in CA-MHB but reduced if tested in either RPMI or in the presence of PaβN (reaching values close to those of PA403). EGTA reduced the MICs of ketolides in CA-MHB and had an additive effect in RPMI. CEM-101 showed a smaller difference in the presence of efflux pump inhibitors.

Example

Several in vivo protocols wherein CEM-101 is repeatedly dosed in toxicology studies in rodents and non human primates have demonstrated tissue levels of CEM-101 between about 17 and about 100× higher than peak plasma levels. CEM-101 accumulated in tissues and concentrations were highest in liver, spleen, lung, and salivary gland. This relationship was confirmed in rodent ADME studies using radiolabeled CEM-101. When administered orally at 100 mg/kg, lung tissue to plasma radioactivity ratios of about 13:1 were observed in male and female animals. After IV dosing at 20 mg/kg, the data was more variable and lung/plasma ratios of 17.6 for males and 6.2 for females were observed. Cmax and AUC ranged from 0.022 μg/mL and 0.04 μg·h/mL to 1.96 μg/mL and 28.60 μg·h/mL across the dose range. The mean CEM-101 tmax increased from 1.5 to 6.0 hours and the mean terminal half-life increased from 2.2 to 7.9 hours over the 50 to 1600 mg dose range.

Example. Tissue Distribution

CEM-101 is well absorbed and distributed to the tissue. In the rat at 250 mg/kg/d, mean lung and liver concentrations 5 of CEM-101 were 17 and 15-fold higher than in plasma. Lung and liver concentrations were 503 and 711-fold higher than plasma concentrations at the 200 mg/kg/d dose in monkeys. Concentrations of CEM-101 in the heart were Example. Activity of CEM-101 Alone and in Combination with Tobramycin and Amikacin, Against *P. aeruginosa*, MRSA, and *B. cepacia*

Cystic fibrosis is a congenital genetic abnormality commonly encountered in the US. As a result of this disease patients, who may live through early to late adulthood, suffer from recurrent bouts of pneumonia caused by *Pseudomonas aeruginosa* (often mucoid), *Burkholderia cepacia*, and MRSA, and other pathogens. The recurrent nature of these infectious attacks leads to multi-resistance and sometimes pan-resistance, with combination therapy the only therapeutic alternative. There is a dearth of new experimental agents active against resistant Gram-negative and Gram-positive strains in general, and CF strains in particular.

CEM-101 is tested against *P. aeruginosa*, MRSA, and *B. cepacia* strains isolated from CF strains isolated at Hershey Medical Center, alone and in combination with amikacin and tobramycin.

Strains.

Two strains each of mucoid *P. aeruginosa* (both pyocyanin positive) and 40 MRSA (only one strain with gold colonies) isolated from patients at a CF clinic were tested. Additionally, 2 *B. cepacia* strains were acquired, from Hershey Medical Center. All strains were identified by standard methods. Only one strain per patient was tested. MLVA was done on all strains to examine clonality, and confirmed that examination is not taking place on only one or a few clones. Strains will be stored in skim milk at −70° C. until use.

Susceptibility Testing.

Original MICs of each strain to CEM-101 and other comparators were tested by CLSI microdilution methodology. Trays were obtained from Trek, Inc., Cleveland, Ohio. Time-kill macrobroth MIC dilution by CLSI was performed for all synergy testing.

Synergy Testing.

Two of the MRSA strains were chosen and tested for synergy, together with the 4 Gram-negative strains mentioned above. Broth macrodilution formed the basis of MICs used in time-kill experiments, as detailed below. The kill kinetics of each drug was tested alone by incubating an initial inoculum of $5 \times 10^5$ to $5 \times 10^6$ cfu/mL with drug concentrations at the MIC, three dilutions above and three dilutions below the MIC (½, ¼ and ⅛×MIC). Viability counts were performed after 0, 3, 6, 12 and 24 h incubation at 37° C. in a shaking water bath by plating onto trypticase soy-5% sheep blood agar plates.

After initial time-kills with compounds alone are performed, CEM-101 was combined with amikacin and tobramycin. Combinations were tested 1-2 dilutions below the MIC (½×MIC and ¼×MIC) of each drug. Inocula and time-kill methodology were as above when the compounds alone are tested. Concentrations in synergy time-kill tests were selected such that one of the two drugs yields a growth curve similar to that of the drug-free control, while the other drug was more active.

MICs were Assayed by Standard Methodology.

Synergy was defined as a $\geq 2$ $\log_{10}$ decrease in cfu/mL between the combination and its most active constituent after 3, 6, 12 and 24 h, with the number of surviving organisms in the presence of the combination $\geq 2$ $\log_{10}$ cfu/mL below the starting inoculum. At least one of the compounds in the combination was present in a concentration which did not significantly affect the growth curve of the organism when used alone. Antagonism was defined as a $\geq 2$ $\log_{10}$ increase in cfu/mL between the combination and its most active constituent after 3, 6, 12 and 24 h, with the number of surviving organisms in the presence of the combination $\geq 2$ $\log_{10}$ cfu/mL above the starting inoculum.

Results.

Each individual strain tested proved to be an individual clone. Compiled *S. aureus* (MRSA) MICs (µg/mL) are listed in Table 3.

TABLE 3

Microdilution MICs (µg/mL) of all compounds against 40 MRSA strains from CF patients.

| Drug | Range | $MIC_{50}$ | $MIC_{90}$ |
|---|---|---|---|
| CEM-101 | 0.06-≥16 | 0.25 | ≥16 |
| Vancomycin | 0.5-1 | 0.5 | 1 |
| Teicoplanin | 0.25-1 | 0.5 | 1 |
| Daptomycin | 0.5-1 | 0.5 | 1 |
| Tigecycline | 0.12-0.25 | 0.12 | 0.25 |
| Azithromycin | 1-≥32 | ≥32 | ≥32 |
| Clarithromycin | 0.25-≥32 | ≥32 | ≥32 |
| Linezolid | 1-4 | 2 | 2 |
| Quinupristin/dalfopristin | 0.25-1 | 0.5 | 1 |

CEM-101 was active (MICs 0.06-0.25) against 21 of the 40 strains (52.5%), with MICs against the remaining organisms ≥16 µg/mL. Vancomycin and teicoplanin were also active at MICs 0.25-1, linezolid at MICs 1-4 and quinupristin/dalfopristin at MICs 0.25-1. Most strains (38 of 40) were resistant (>32) to azithromycin and clarithromycin. Microbroth MICs for the 4 Gram-negative rods are presented in Tables 4 and 5, and time-kill macrobroth MIC data are shown in Table 6.

TABLE 4

Macrobroth Dilution MICs (µg/mL) of all compounds against 2 *P. aeruginosa* strains from cystic fibrosis patients.

| Drug | Range |
|---|---|
| CEM-101 | 64 |
| Amikacin | 2-8 |
| Tobramycin | 0.25-1.0 |

TABLE 5

Macrobroth Dilution MICs (µg/mL) of all compounds against 2 *B. cepacia* strains from cystic fibrosis patients.

| Drug | Range |
|---|---|
| CEM-101 | 8-32 |
| Amikacin | 256 |
| Tobramycin | 128 |

TABLE 6

Time-kill Macrobroth MICs (µg/mL) of all compounds against 6 strains from cystic fibrosis patients.

| Strain | CEM-101 | Tobramycin | Amikacin |
|---|---|---|---|
| SA 2230 | 0.125 | 4.0 | 32.0 |
| SA 2232 | 0.125 | NT[a] | 64.0 |
| PSAR 461 | 64.0 | 2.0 | 8.0 |
| PSAR 468 | 32.0 | 1.0 | 4.0 |
| BCEP 953 | 8.0 | 128 | 512 |
| BCEP 954 | 32.0 | 128 | 256 |

[a]NT; not tested

Synergy time-kill data are shown in Tables 7 and 8.

TABLE 7

Results of In Vitro Antimicrobial Combinations with CEM101 Studied by Time-kill

| | CEM-101/Tobramycin[c] | | | | CEM-101/Amikacin | | | |
|---|---|---|---|---|---|---|---|---|
| | 3 h[a] | 6 h[a] | 12 h[a] | 24 h[a] | 3 h | 6 h | 12 h | 24 h |
| Synergy | 0[b] | 0 | 0 | 1 | 0 | 0 | 0 | 1 |
| Indifference | 5 | 5 | 4 | 4 | 6 | 6 | 4 | 5 |
| Antagonism | 0 | 0 | 1 | 0 | 0 | 0 | 2 | 0 |

[a]time-point (hours)
[b]number of strains (strains tested)
[c]one strain (MRSA 2232) not tested (MIC > 512 µg/mL)

TABLE 8

Results of In Vitro Antimicrobial Combinations with CEM101 Studied by Time-kill

| | CEM-101/Tobramycin | | | | CEM-101/Amikacin | | | |
|---|---|---|---|---|---|---|---|---|
| | 3 h[a] | 6 h[a] | 12 h[a] | 24 h[a] | 3 h | 6 h | 12 h | 24 h |
| SA2230 | IND | IND | IND | SYN[b] (0.03/2) | IND | IND | IND | IND |
| SA2232 | NT[c] | NT | NT | NT | IND | IND | IND | SYN (0.06/32) |
| PSAR461 | IND | IND | IND | IND | IND | IND | ANT | IND |
| PSAR468 | IND | IND | IND | IND | IND | IND | IND | IND |

TABLE 8-continued

Results of In Vitro Antimicrobial Combinations
with CEM101 Studied by Time-kill

| | CEM-101/Tobramycin | | | | CEM-101/Amikacin | | | |
|---|---|---|---|---|---|---|---|---|
| | 3 h[a] | 6 h[a] | 12 h[a] | 24 h[a] | 3 h | 6 h | 12 h | 24 h |
| BCEP953 | IND | IND | ANT[b] | IND | IND | IND | ANT | IND |
| BCEP954 | IND | IND | IND | IND | IND | IND | IND | IND |

[a]time-point (hours)
[b]IND—indifference; SYN—synergy; ANT—antagonism
[c]NT; not tested (MIC > 512 µg/mL)

Briefly, synergy was found with CEM-101/tobramycin at (0.03/2) concentration at 24 h for one MRSA strain and at 0.06/32 µg/mL for CEM-101/amikacin at 24 h for the second MRSA strain. All other time points and combinations were indifferent for the 2 MRSA strains. One strain of MRSA was not tested with tobramycin in combination because of its very high MIC (>512 µg/mL). One of the 2 *P. aeruginosa* strains showed antagonism at 12 h with the CEM-101/amikacin combination (16/4 µg/mL). All other time points and combinations were indifferent with the 2 *P. aeruginosa* strains. One *B. cepacia* strain was antagonistic at 12 h with the CEM-101/tobramycin and CEM-101/amikacin combinations (2/64 and 2/256 µg/mL, respectively). The 2 *B. cepacia* strains were indifferent at all other time points and drug combinations.

No correlation between pigment and any MRSA results was found. When both mucoid *P. aeruginosa* strains were subcultured for a few days, viscosity disappeared but reappeared when they were re-exposed to all combinations. CEM-101 showed low MICs against approximately ½ of MRSA strains tested. Synergy was not found in the Gram negative rods tested. For MRSA, clinically achievable synergy was observed with strain SA 2230, with CEM-101 combined with tobramycin. Synergy against MRSA SA 2230 is shown in FIG. 1.

Example. Intrapulmonary Penetration of CEM-101 in Healthy Adult Subjects

CEM-101 is evaluated for the treatment of patients with community-acquired bacterial pneumonia. The penetration of CEM-101 into the epithelial lining fluid (ELF) and alveolar macrophages (AM) is assessed in a Phase 1 clinical study.

Methods:

30 subjects received 400 mg of CEM-101 orally daily for 5 days. On Day 5, each subject underwent a single bronchoscopy and bronchoalveolar lavage at 1 of 5 time points (3, 6, 9, 12 or 24 h post-dose) to obtain ELF and AM samples (6 subjects/time point). Plasma samples were collected pre-dose on Days 1 to 5 and serially post-dose on Day 5 and 6. The samples collected were assayed for CEM-101 using LC/MS/MS. Urea in the plasma and ELF was used to correct the ELF CEM-101 concentrations. Noncompartmental pharmacokinetic (PK) analysis using the median concentrations at each time point was used to calculate Day 5 AUC0-24. In addition, a population PK model (PPM) was used to determine Day 5 AUC0-24 for each subject in plasma and ELF. Intrapulmonary penetration of CEM-101 into the ELF and AM was determined by dividing the Day 5 AUC0-24 of each matrix by the Day 5 plasma AUC0-24.

Results:

CEM-101 penetrated well into ELF and AM. CEM-101 achieved higher exposures in ELF (>8 times) and AM (>180 times) compared to plasma concentrations during the 24 hour period after drug administration in healthy adults. CEM-101 provides a good intrapulmonary penetration profile for the treatment of bacterial pathogens associated with lower respiratory tract infections.

Example. Pharmacokinetic-Pharmacodynamic (PK-PD) Analysis of CEM-101 Against *Streptococcus pneumoniae* Using Data from a Murine-Lung Infection Model Using a murine-lung infection model, epithelial lining fluid (ELF) and plasma PK-PD measures most closely associated with CEM-101 efficacy against *S. pneumoniae* and targets based on PK-PD relationships for such indices were identified.

Methods:

CEM-101 PK data were obtained from healthy mice administered single CEM-101 doses ranging from 0.625 to 40 mg/kg. Plasma and ELF were collected over 24 h (3 mice/time point) and assayed for CEM-101. Urea in plasma and ELF was used to correct ELF concentrations. Neutropenic mice infected with 108 CFU of 1 of 5 *S. pneumoniae* isolates via inhalation were administered daily CEM-101 doses (0.156 to 160 mg/kg) via oral gavage. Dose-fractionation was performed for 1 isolate; CEM-101 was administered to the other 4 isolates as a Q6h or Q12h regimen. PK and PK-PD were evaluated using S-ADAPT 1.56.

Results:

A 3-compartment model with a parallel first-order and capacity-limited clearance and a capacity-limited first pass effect with fitted lag-times best described the plasma and ELF data ($r2=0.98$ and $0.83$ for observed vs fitted concentrations, respectively). ELF to total- and free-drug (f) plasma (based on protein binding of 91.8% in mice) AUC0-24 ratios were 0.22 and 2.7, respectively. ELF and f plasma AUC0-24:MIC ratios were most predictive of efficacy ($r2=0.85$ for ELF and f plasma). ELF and f plasma AUC0-24:MIC ratios associated with net bacterial stasis and a 1- and 2-log 10 CFU reduction from baseline were 1.26 and 1.65, 15.1 and 6.31, and 59.8 and 12.8, respectively. AUC0-24:MIC ratio was the PK-PD index most predictive of efficacy for CEM-101. PK-PD targets based on these relationships will inform dose selection for future clinical studies.

Example. Compounds Described Herein Exhibit Potent Anti-Inflammatory Activity

Cells.

The human monocytic cell line U937 was obtained from the American Type Culture Collection (ATCC, Rockville, Md.). PBMCs from COPD patients were obtained from Brompton hospital and separated by AccuSPIN (Sigma-Aldrich). Cells were cultured in complete growth medium (RPMI 1640) (Sigma-Aldrich) supplemented with 10% fetal bovine serum (FBS) and 1% L-glutamine at 37° C. in a humidified atmosphere with 5% $CO_2$. U937 cells were differentiated into adherent macrophage-like morphology by exposure to PMA (50 ng/mL) for 48 hrs in complete growth medium. Cell viability was assessed microscopically by trypan blue staining. Cell toxicity was determined by MTT assay as needed. This study was approved by the ethics committee of the Royal Brompton Hospitals, and all subjects gave written informed consent.

Cell Lysis.

Whole cell extracts were prepared as previously described (Kobayashi et al., 2011). Briefly, cell protein extracts were prepared using modified RIPA buffer (50 mM Tris HCl pH 7.4, 0.5% NP-40, 0.25% Na-deoxycholate, 150 mM NaCl with freshly added complete protease inhibitor cocktail (Roche, Mannheim, Germany)). Protein concentration was determined using the BCA Protein Assay (Thermo Fisher Scientific, Waltham, Mass.).

Cytokine ELISA.

TNFα and IL-8 concentrations in the supernatant of cell cultures were determined by sandwich ELISA according to the manufacturer's instructions (R&D Systems Europe, Abingdon, UK).

Zymography.

MMP9 enzyme activity was measured by gelatin zymography. Cell culture supernatants were diluted with equal amount of Laemli sample buffer (Bio-Rad, Hertfordshire, UK) and loaded on a Novex® 10% Zymogram (Gelatin) gel (Invitrogen Ltd, Paisley, UK). After electrophoresis, gels were incubated and rinsed with Novex® zymogram renaturing buffer (Invitrogen) for 30 min at room temperature. The gels were then rinsed in Novex® zymogram developing buffer (Invitrogen) for 30 min at room temperature prior to overnight incubation in the developing buffer at 37° C. After incubation, the gels were stained using a Colloidal Blue Staining Kit (Invitrogen) to visualize the zymogen bands.

NF-κB Activity.

The activation of NF-κB (p65 binding activity to NF-κB binding sequence) was determined using a TransAM NF-κB p65 Assay kit (Active Motif, Inc., Carlsbad, Calif.) according to the manufacturer's instruction. Whole cell extracts were prepared from PMA-differentiated U937 cells, and 20 μL of each extract was used for this study. Results were determined by measuring the spectrophotometric absorbance at 450 nm with a reference wavelength of 655 nm.

Statistical Analysis.

The results were expressed as the mean±SEM. Comparisons of data in two groups were performed using the Student's t test or the Wilcoxon signed rank test. Multiple comparisons were made by one-way ANOVA with post hoc test (Dunnett's) as appropriate. The difference was considered significant at p<0.05. $IC_{50}$ values (50% inhibitory concentration) for macrolides for production of cytokines or MMP9 were calculated using Prism 4.0 (GraphPad Software Inc., San Diego, Calif.).

Anti-Inflammatory Effects of CEM-101 in U937 Cells.

Figure 3:
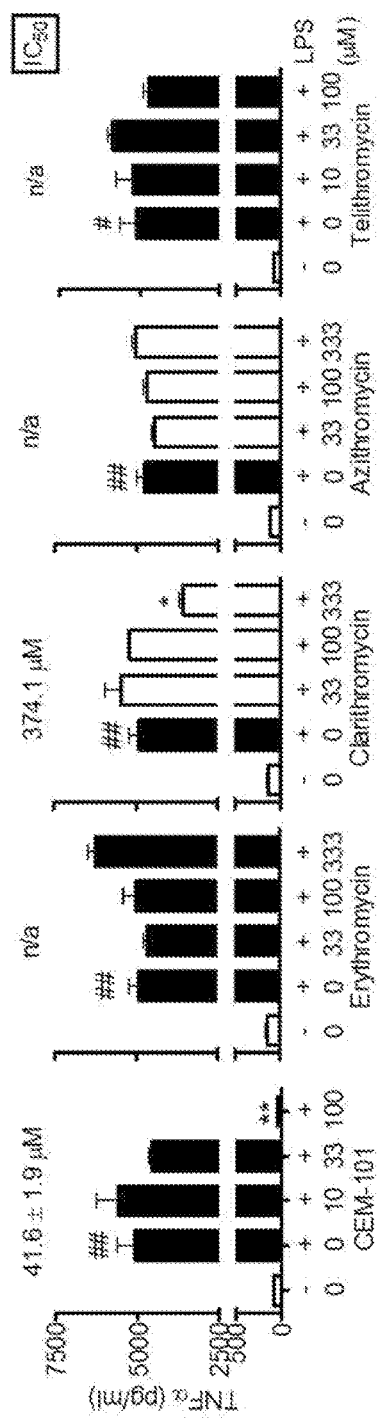
FIG. 3 shows the effect of various macrolides on LPS-induced TNFα production. Effects of macrolides on lipopolysaccharide (LPS)-induced TNFα release in PMA-differentiated U937 cells. Cells were pretreated with CEM-101 (10 to 100 μM) or erythromycin, clarithromycin, azithromycin, or telithromycin (33 to 333 μM) for 1 h, followed by LPS (100 ng/mL) stimulation for 4 h. LPS-induced TNFα release was evaluated by ELISA. Values represent means of three experiments±SEM. $^{\#\#\#}p<0.01$ (vs. non-treatment control), $*p<0.05$, $**p<0.01$ (vs. treatment with LPS only).
Figure 4:
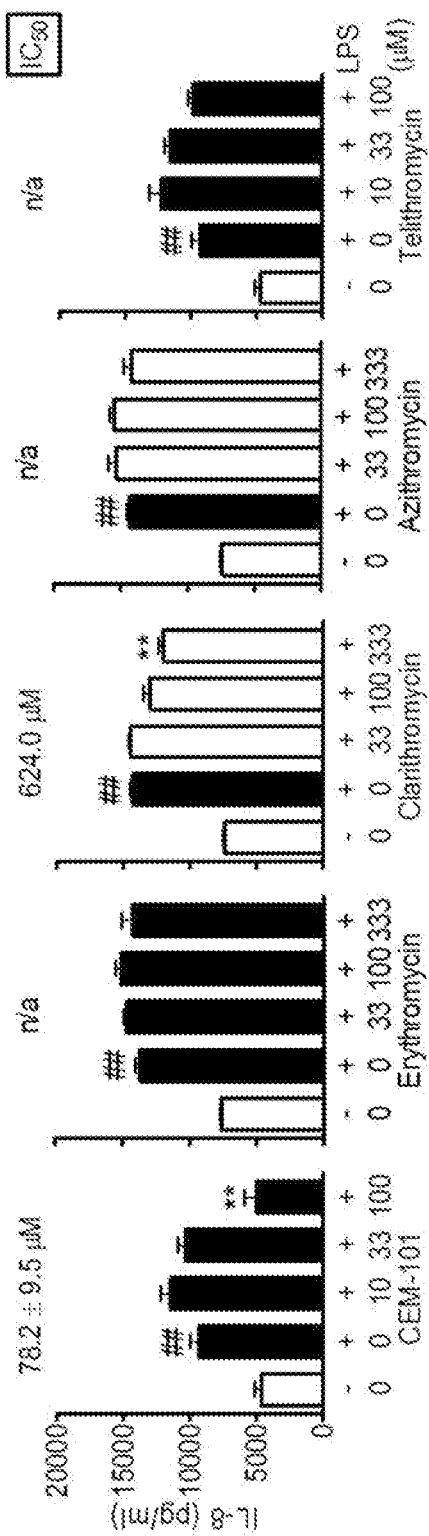
FIG. 4 shows the effect of various macrolides on LPS-induced IL-8 production. Effects of macrolides on lipopolysaccharide (LPS)-induced CXCL8 release in PMA-differentiated U937 cells. Cells were pretreated with CEM-101 (10 to 100 μM) or erythromycin, clarithromycin, azithromycin, or telithromycin (33 to 333 μM) for 1 h, followed by LPS (100 ng/mL) stimulation for 4 h. LPS-induced CXCL8 release was evaluated by ELISA. Values represent means of three experiments±SEM. $^{\#\#\#}p<0.01$ (vs. non-treatment control), $*p<0.05$, $**p<0.01$ (vs. treatment with LPS only).

LPS significantly increased TNFα and IL-8 production in PMA-differentiated U937 cells (TNFα, 63.1±2.6 fold in LPS vs. non-stimulated; and CXCL8, 2.0±0.1 fold in LPS vs. non-stimulated cells, n=3). CEM-101 significantly inhibited both TNFα and CXCL8 at 100 μM (FIGS. 3 and 4). Although clarithromycin showed modest effects on both TNFα and IL-8 production at a higher concentration (333 μM), erythromycin and azithromycin did not inhibit them. Telithromycin at 100 μM did not inhibit production of TNFα and CXCL8. The $IC_{50}$ values for CEM-101 on TNFα and CXCL8 release were 41.6±1.9 μM and 78.2±9.5 μM, respectively, and were superior to those for clarithromycin ($IC_{50}$, 426.3±63.9 μM for TNFα and 506.5±44.0 μM for CXCL8) (Table 9).

Figure 2:
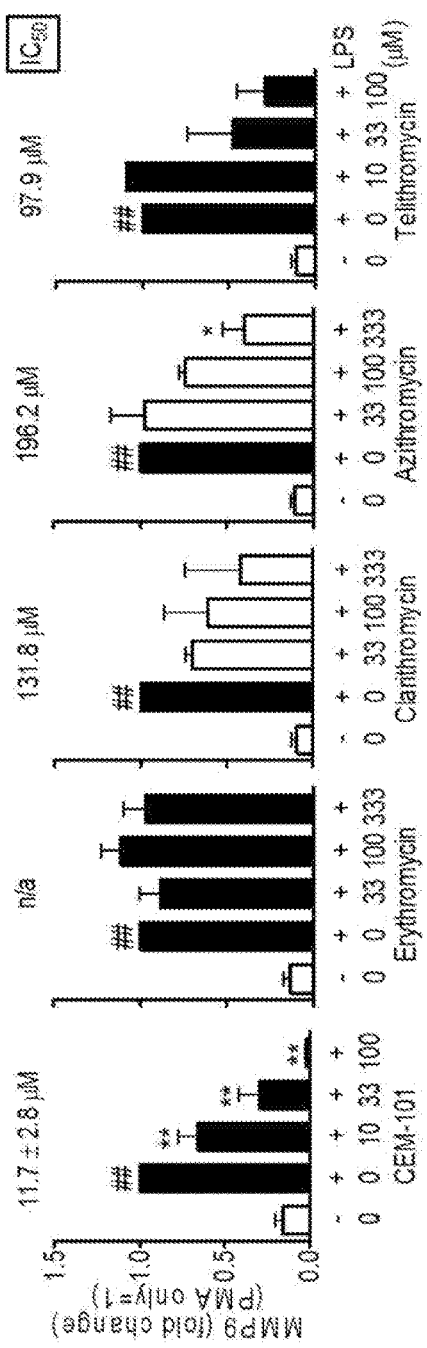
FIG. 2 shows the effect of various macrolides on PMA-induced MMP9 production. Effects of macrolides on phorbol 12-myristate 13-acetate (PMA)-induced MMP9 activation in U937 cells. Cells were pretreated with CEM-101 (10 to 100 μM) or erythromycin, clarithromycin, azithromycin, or telithromycin (33 to 333 μM) for 1 h, followed by PMA (50 ng/mL) treatment for 48 h. After 48 h supernatants were collected for zymography. MMP9 enzyme activity was measured by gelatin zymography. Data are expressed relative to standard. Values represent means of four experiments for CEM-101 and three experiments for each of erythromycin, clarithromycin, azithromycin, and telithromycin, ±SEM. $^{\#\#\#}p<0.01$ (vs. non-treatment control), $*p<0.05$, $**p<0.01$ (vs. treatment with PMA only).

The effects of macrolides on MMP9 activity was also investigated, which were clearly elevated by PMA stimulation in U937 cells (9.9±2.0 fold in PMA vs. non-stimulation, n=3). CEM-101 remarkably reduced MMP9 activity, with an $IC_{50}$ of 14.9±3.1 μM (FIG. 2 and Table 9). In contrast, clarithromycin and azithromycin showed 10-fold lower inhibitory effects than CEM-101 whereas erythromycin showed no effect (FIG. 2 and Table 9). Telithromycin also inhibited MMP9 activity, although to lesser extent than CEM-101, with an $IC_{50}$ of 97.9 μM.

TABLE 9

Effect of macrolides on inhibition of LPS-induced IL-8 and TNFα release, and PMA-induced MMP9 activation in U937 cells.

| | $IC_{50}$ (μM) | | | | |
|---|---|---|---|---|---|
| | Solithromycin | Erythromycin | Clarithromycin | Azithromycin | Telithromycin |
| LPS-induce IL-8 release | 78.2 | NE at 333 μM | 506.5 | NE at 333 μM | NE at 100 μM |
| LPS-induced TNFα release | 41.6 | NE at 333 μM | 426.3 | NE at 333 μM | NE at 100 μM |
| PMA-induced MMP9 activation | 14.9 | NE at 333 μM | 118.0 | 212.1 | 97.9 |

NE: no effect

What is claimed is:

1. A method for treating cystic fibrosis in a host animal, the method comprising administering to the host animal a therapeutically effective amount of one or more compounds of the formula

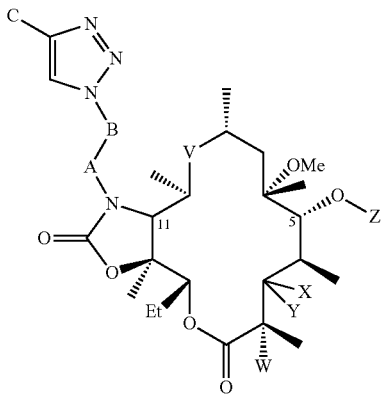

or pharmaceutically acceptable salts thereof, wherein:
X is H; and Y is $OR_7$; where $R_7$ is a monosaccharide or disaccharide, or a derivative thereof; or X and Y are taken together with the attached carbon to form carbonyl;
Z is a desosamine;
V is C(O), or C(=$NR_{11}$), wherein $R_{11}$ is hydroxy or alkoxy;
W is H, F, Cl, Br, I, or OH;
A is $CH_2$, C(O), C(O)O, C(O)NH, S(O)$_2$, S(O)$_2$NH, or C(O)NHS(O)$_2$;
B is saturated $C_0$-$C_{10}$; or B is unsaturated $C_2$-$C_{10}$; and
C is cycloalkyl, cycloheteroalkyl, aryl, arylalkyl, heteroaryl, or heteroarylalkyl, each of which is optionally substituted;
where the compound is administered by inhalation to the endobronchial space of the patient.

2. The method of claim 1 wherein X and Y are taken together with the attached carbon to form carbonyl.

3. The method of claim 1 wherein V is C(O).

4. The method of claim 1 wherein W is H or F.

5. The method of claim 1 wherein W is F.

6. The method of claim 1 wherein A is $CH_2$.

7. The method of claim 1 wherein B is $(CH_2)_n$.

8. The method of claim 1 wherein n is an integer from 2 to 4.

9. The method of claim 1 wherein n is 3.

10. The method of claim 1 wherein C is aryl, arylalkyl, heteroaryl, or heteroarylalkyl, each of which is optionally substituted.

11. The method of claim 1 wherein C is aryl or heteroarylalkyl, each of which is optionally substituted.

12. The method of claim 1 wherein C is substituted aryl.

13. The method of claim 1 wherein the compound is solithromycin, or a pharmaceutically acceptable salt thereof.

14. The method of claim 1 wherein the host animal is immunocompromised.

15. The method of claim 1 wherein the disease is caused by one or more clarithromycin resistant bacteria.

16. The method of claim 1 further comprising administering a therapeutically effective amount of an aminoglycoside.

17. The method of claim 1 further comprising the step of administering a therapeutically effective amount of a fluoroquinolone antibiotic.

18. A composition comprising one or more compounds of the formula

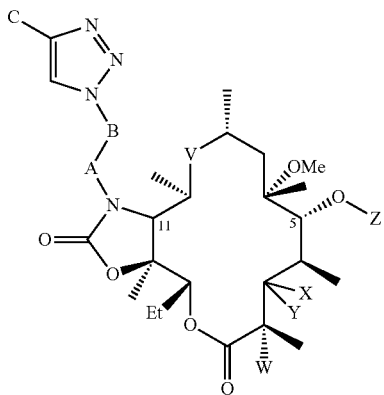

or pharmaceutically acceptable salts thereof, wherein:

X is H; and Y is $OR_7$; where $R_7$ is a monosaccharide or disaccharide, or a derivative thereof; or X and Y are taken together with the attached carbon to form carbonyl;

Z is a desosamine;

V is C(O), or C(=$NR_{11}$), wherein $R_{11}$ is hydroxy or alkoxy;

W is H, F, Cl, Br, I, or OH;

A is $CH_2$, C(O), C(O)O, C(O)NH, $S(O)_2$, $S(O)_2NH$, or $C(O)NHS(O)_2$;

B is $(CH_2)_n$ where n is an integer in the range from 0 to about 10, or B is $C_2$-$C_{10}$ alkenyl or alkynyl; and C is cycloalkyl, cycloheteroalkyl, aryl, arylalkyl, heteroaryl, or heteroarylalkyl, each of which is optionally substituted;

where the composition is in the form of a powder adapted for administration by inhalation.

19. The method of claim 1 wherein the compound is solithromycin.

20. The composition of claim 18 wherein X and Y are taken together with the attached carbon to form carbonyl; and V is C(O).

21. The composition of claim 18 wherein W is H or F.

22. The composition of claim 18 wherein A is $CH_2$, B is $(CH_2)_n$, and n is an integer from 2 to 4.

23. The composition of claim 18 wherein C is substituted aryl.

24. The composition of claim 18 wherein the compound is solithromycin, or a pharmaceutically acceptable salt thereof.

25. The composition of claim 18 wherein the compound is solithromycin.

26. The method of claim 13 wherein the host animal is human.

27. The method of claim 19 wherein the host animal is human.

* * * * *